(12) United States Patent
Tada et al.

(10) Patent No.: US 10,539,535 B2
(45) Date of Patent: Jan. 21, 2020

(54) DEFECT MEASUREMENT METHOD, DEFECT MEASUREMENT DEVICE, AND TESTING PROBE

(71) Applicant: SUMITOMO CHEMICAL COMPANY, LIMITED, Tokyo (JP)

(72) Inventors: Toyokazu Tada, Niihama (JP); Hidehiko Suetsugu, Niihama (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 29 days.

(21) Appl. No.: 15/744,700

(22) PCT Filed: Jun. 15, 2016

(86) PCT No.: PCT/JP2016/067808
§ 371 (c)(1),
(2) Date: Jan. 12, 2018

(87) PCT Pub. No.: WO2017/010215
PCT Pub. Date: Jan. 19, 2017

(65) Prior Publication Data
US 2018/0217097 A1    Aug. 2, 2018

(30) Foreign Application Priority Data
Jul. 16, 2015    (JP) ................................ 2015-142390

(51) Int. Cl.
*G01N 27/90*    (2006.01)
(52) U.S. Cl.
CPC ................................. *G01N 27/902* (2013.01)

(58) Field of Classification Search
CPC ........................... G01N 27/902; G01N 27/82
See application file for complete search history.

(56) References Cited

U.S. PATENT DOCUMENTS 3,940,689 A    2/1976  Johnson, Jr.
4,659,991 A *  4/1987  Weischedel ............ G01N 27/82
                                                   324/241
(Continued)

FOREIGN PATENT DOCUMENTS

CN    102798660 A    11/2012
CN    103149272 A    6/2013
(Continued)

OTHER PUBLICATIONS

Japanese Office Action, dated Feb. 12, 2019, for Japanese Application No. 2015-142390, with a partial English translation.

(Continued)

*Primary Examiner* — Dominic E Hawkins
(74) *Attorney, Agent, or Firm* — Birch, Stewart, Kolasch & Birch, LLP

(57) ABSTRACT

The present invention quickly carries out quantitative evaluation of a defect of a magnetic member. An inspection probe (100), which includes: a third magnet (4) polarized in a direction intersecting a counter surface facing a magnetic member; a Hall element (11) that detects a density of a magnetic flux passing through the third magnet (4) and the magnetic member, is used to apply, to an output signal from the Hall element (11), an evaluation algorithm which is selected according to whether a defective surface is a front surface or a back surface.

14 Claims, 13 Drawing Sheets

(56) References Cited

U.S. PATENT DOCUMENTS

| | | | |
|---|---|---|---|
| 4,727,321 A | 2/1988 | Hüschelrath | |
| 4,789,827 A * | 12/1988 | Bergander | G01N 27/82 324/220 |
| 6,150,809 A | 11/2000 | Tiernan et al. | |
| 6,967,478 B2 * | 11/2005 | Wayman | G01N 27/82 324/235 |
| 9,030,195 B2 * | 5/2015 | Gies | G01N 27/82 324/221 |
| 9,287,029 B1 * | 3/2016 | Colich | H01F 7/0289 |
| 9,678,041 B2 * | 6/2017 | Schein, Jr. | G01N 27/82 |
| 2002/0130659 A1 * | 9/2002 | Wincheski | G01N 27/9033 324/235 |
| 2005/0200354 A1 | 9/2005 | Edwin et al. | |
| 2006/0202700 A1 | 9/2006 | Barolak et al. | |
| 2010/0148766 A1 * | 6/2010 | Weischedel | G01N 27/9033 324/238 |
| 2012/0007596 A1 * | 1/2012 | Hashimoto | G01N 27/902 324/240 |
| 2013/0174757 A1 * | 7/2013 | Post | B60L 13/04 104/283 |
| 2015/0233868 A1 * | 8/2015 | Zec | G01N 27/825 324/240 |
| 2015/0239708 A1 * | 8/2015 | Palazzola | B66B 5/0025 187/254 |
| 2015/0323502 A1 * | 11/2015 | Suetsugu | G01N 27/902 324/240 |
| 2015/0346153 A1 * | 12/2015 | Boyd | G01N 1/28 324/240 |

FOREIGN PATENT DOCUMENTS

| | | |
|---|---|---|
| CN | 103175891 A | 6/2013 |
| GB | 2262346 A | 6/1993 |
| JP | 50-94987 A | 7/1975 |
| JP | 63-40850 A | 2/1988 |
| JP | 63-133054 A | 6/1988 |
| JP | 2-210256 A | 8/1990 |
| JP | 3-53155 A | 3/1991 |
| JP | 5-164745 A | 6/1993 |
| JP | 8-136508 A | 5/1996 |
| JP | 9-188496 A | 7/1997 |
| JP | 2002-5893 A | 1/2002 |
| JP | 2004-212161 A | 7/2004 |
| JP | 2004-279372 A | 10/2004 |
| JP | 2009-122074 A | 6/2009 |
| JP | 2009-287931 A | 12/2009 |
| JP | 2010-127854 A | 6/2010 |
| JP | 2010-237186 A | 10/2010 |
| JP | 2012-103177 A | 5/2012 |
| JP | 5169983 B2 | 3/2013 |
| RU | 2440493 C1 | 1/2012 |

OTHER PUBLICATIONS

International Preliminary Report on Patentability and English translation of the Written Opinion of the International Searching Authority (Forms PCT/IB/373 and PCT/ISA/237) for International Application No. PCT/JP2016/067807, dated Jan. 16, 2018.

International Preliminary Report on Patentability and English translation of the Written Opinion of the International Searching Authority (Forms PCT/IB/373 and PCT/ISA/237) for International Application No. PCT/JP2016/067808, dated Jan. 16, 2018.

International Search Report (Form PCT/ISA/210) for International Application No. PCT/JP2016/067807, dated Sep. 13, 2016, with English translation.

International Search Report (Form PCT/ISA/210) for International Application No. PCT/JP2016/067808, dated Aug. 30, 2016, with English translation.

Japanese Office Action, dated Oct. 2, 2018, for Japanese Application No. 2015-142389, along with an English translation.

Office Action issued in the Singaporean Patent Application No. 11201800262Y dated Oct. 2, 2018.

Office Action issued in the Singaporean Patent Application No. 11201800264Q dated Oct. 5, 2018.

Extended European Search Report, dated Nov. 28, 2018, for European Application No. 16824194.1.

European Patent Office Communication and extended search report issued in the corresponding European Patent Application No. 16824195.8 dated Feb. 25, 2019.

Suetsugu et al., "Development and Application of Non-Destructive Evaluation Technology for Chemical Equipment Materials," Sumitomo Kagaku, 2014, pp. 1-15.

U.S. Office Action issued in U.S. Appl. No. 15/743,444 dated Apr. 1, 2019.

U.S. Office Action, dated Jul. 16, 2019, for U.S. Appl. No. 15/743,444.

* cited by examiner

DEFECT MEASUREMENT METHOD, DEFECT MEASUREMENT DEVICE, AND TESTING PROBE

TECHNICAL FIELD

The present invention relates to (i) a method and a device for measuring a defect of a member made of a magnetic material and (iii) an inspection probe for use in measurement of the defect.

BACKGROUND ART

Known examples of a conventional inspection method for investigating the presence/absence of a defect in a magnetic member such as thinning or crack encompass (i) magnetization eddy current testing (magnetization ECT (Eddy Current Testing)) disclosed in Patent Literature 1 and the like and (ii) a magnetic flux leakage (MFL) disclosed in Patent Literature 2 and the like.

Known examples of a method of quantitatively measuring a depth or the like of a defect of a magnetic member encompass a submersion rotary ultrasonic thickness measuring method (IRIS; Internal Rotary Inspection Systems).

CITATION LIST

Patent Literature

[Patent Literature 1]
Japanese Patent No. 5169983 (Publication Date: Nov. 18, 2010)
[Patent Literature 2]
Japanese Patent Application Publication Tokukai No. 2004-212161 (Publication date: Jul. 29, 2004)

SUMMARY OF INVENTION

Technical Problem

However, although a magnetization eddy current flaw detection test and a magnetic flux leakage allows for inspection of the presence/absence of a defect, these methods unfortunately do not make it possible to quantitatively measure, with accuracy, a depth or the like of the defect.

In addition, although a submersion rotary ultrasonic thickness measuring method allows for highly accurate quantitative measurement of a depth or the like of a defect, this method unfortunately takes time for inspection.

The present invention has been made in view of the problems, and it is an object of the present invention to quickly carry out quantitative evaluation of a defect of a magnetic member.

Solution to Problem

A defect measuring method in accordance with an aspect of the present invention is a method of measuring a defect of a magnetic member, including the steps of: (A) measuring an output from a magnetic sensor with use of an inspection probe including a magnet and the magnetic sensor which is provided on a magnetic circuit formed by the magnet and the magnetic member and which detects a density of a magnetic flux flowing through the magnetic circuit; (B) judging whether the defect is (i) a front surface defect occurring to a front surface of the magnetic member, which front surface is a counter surface facing the inspection probe or (ii) a back surface defect occurring to a back surface of the magnetic member, which back surface is opposite the counter surface; and (C) quantitatively evaluating the defect of the magnetic member by applying, to an output signal from the magnetic sensor, an evaluation algorithm which is selected from evaluation algorithms set in advance for the respective ones of the front surface defect and the back surface defect and which corresponds to a result of the judging in the step (B).

A defect measuring device in accordance with an aspect of the present invention is a defect measuring device which measures a defect of a magnetic member, including: an inspection probe including a magnet and a magnetic sensor which is provided on a magnetic circuit formed by the magnet and the magnetic member and which detects a density of a magnetic flux flowing through the magnetic circuit; and a magnetic flux resistance computing section which is capable of quantitatively evaluating the defect of the magnetic member in accordance with an output signal from the magnetic sensor, the magnetic flux resistance computing section being capable of quantitatively evaluating the defect of the magnetic member by applying, to the output signal, an evaluation algorithm which is selected according to whether (i) the defect is formed on a front surface of the magnetic member, which front surface is a counter surface facing the inspection probe or (ii) the defect is formed on a back surface which is opposite the counter surface.

An inspection probe in accordance with an aspect of the present invention is an inspection probe which inspects a defect of a magnetic member, including: a plurality of magnets provided so as to form a Halbach array along a counter surface of the inspection probe, which counter surface faces the magnetic member; an eddy current flaw sensor provided at a center portion of the Halbach array of the plurality of magnets; and a magnetic sensor which (i) is provided on a magnetic circuit formed by the magnetic member and a magnet that is provided at an end part of the Halbach array of the plurality of magnets and (ii) detects a density of a magnetic flux flowing through the magnetic circuit.

Advantageous Effects of Invention

With a defect measuring method, a defect measuring device, and an inspection probe in accordance with an embodiment of the present invention, it is thus possible to quickly carry out a quantitative evaluation of a defect of a magnetic member.

Figure 7:
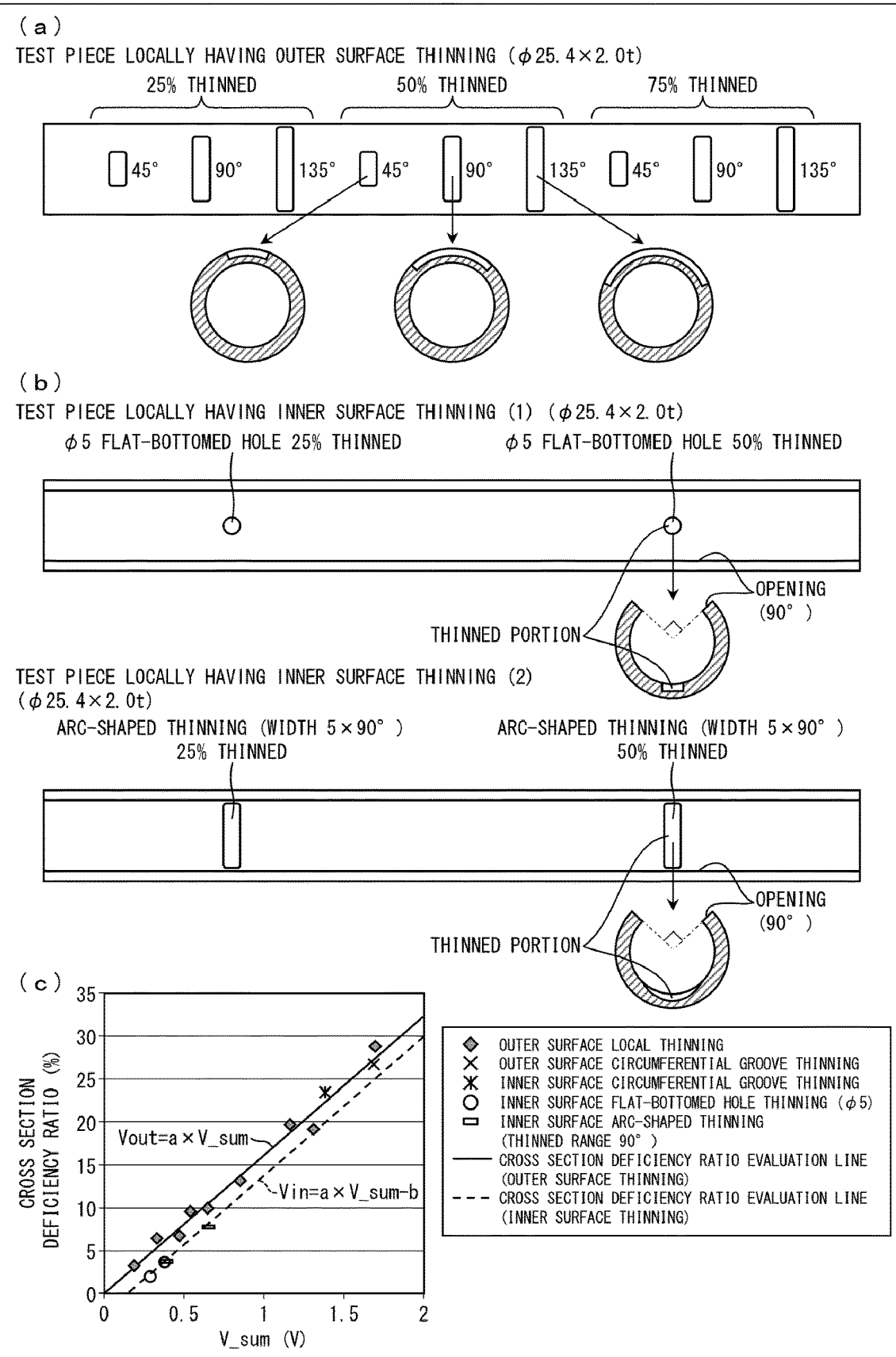

(a) of FIG. 7 is a view for describing an example of test pieces having a plurality of pieces of outer surface thinning. (b) of FIG. 7 is a view for describing examples of test pieces having a plurality of pieces of inner surface thinning. (c) of FIG. 7 is a graph showing relationships between (i) combined values of output signals from the respective Hall elements, which combined values are obtained by measuring the test pieces by the magnetic flux resistance and (ii) actual cross section deficiency ratios of the thinning of the respective test pieces.

Figure 8:
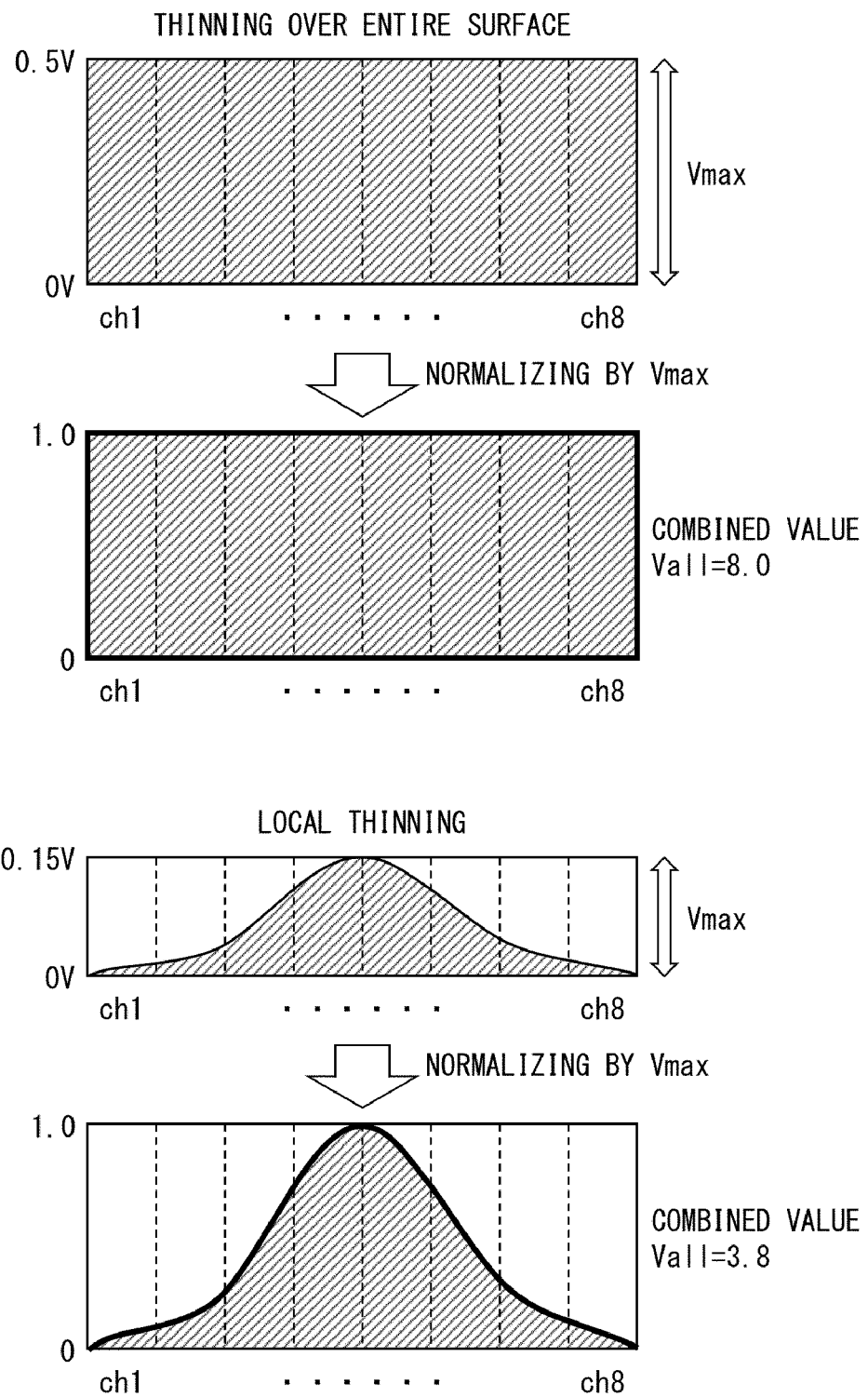

FIG. 8 is a view for describing an example of output voltage values from the Hall elements and shape parameters in a case where flaw detection of thinning over an entire surface and of local thinning is carried out by the thinning measuring device in accordance with the embodiment of the present invention.

Figure 9:
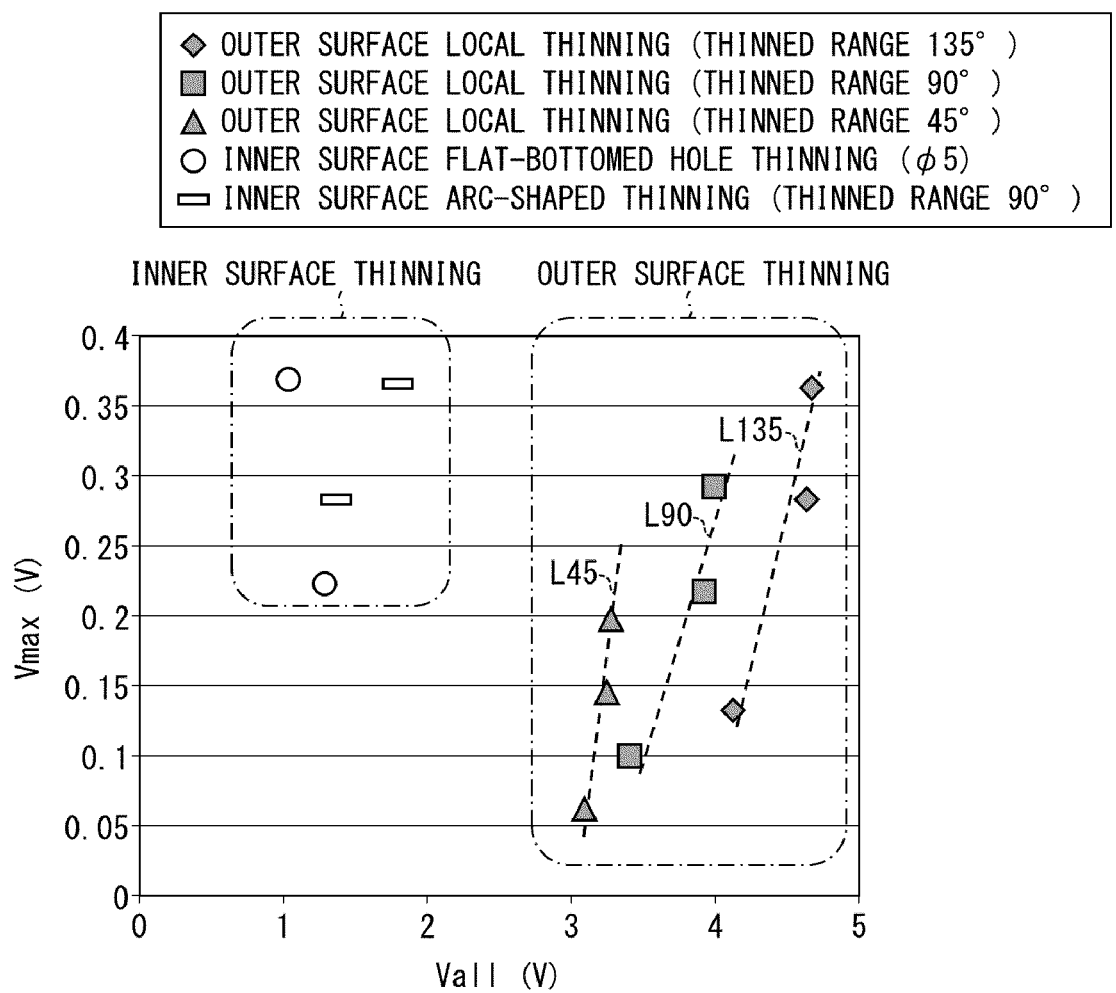

FIG. 9 is a graph showing Vmax and Vall which are calculated based on the results of the flaw detection of the test pieces illustrated in (a) and (b) of FIG. 7.

Figure 10:
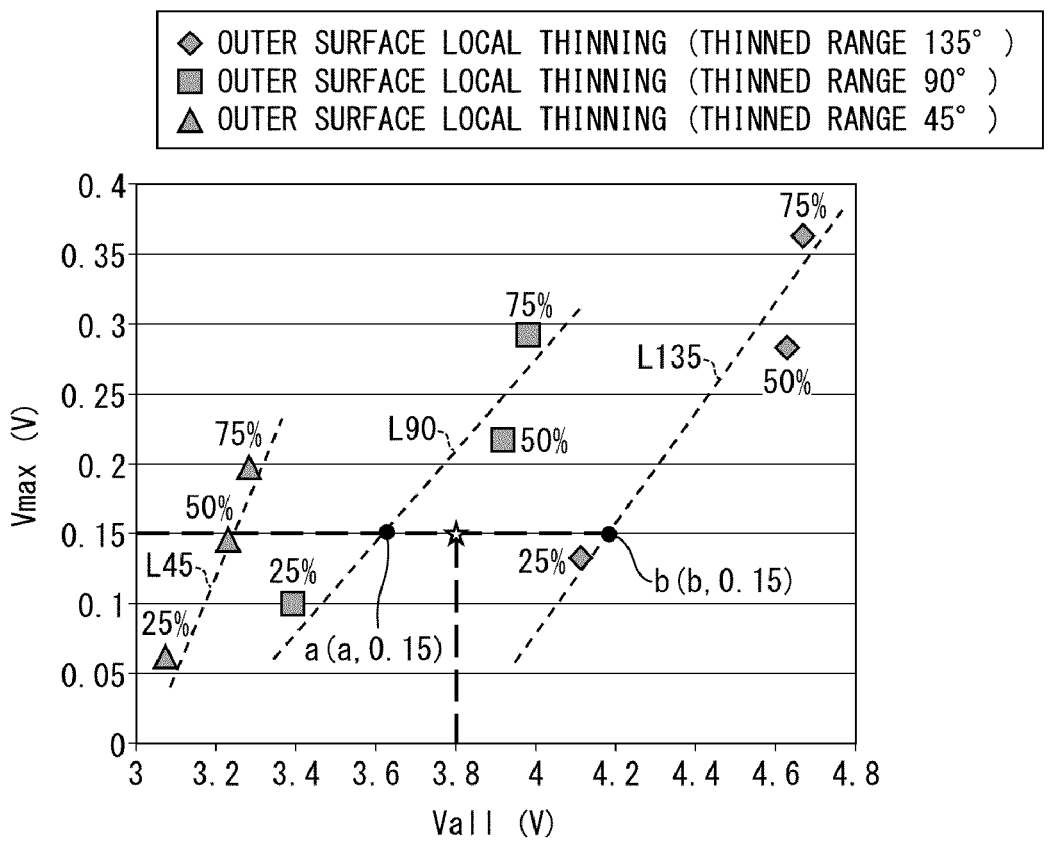

FIG. 10 is a graph in which data, of all of pieces of data shown in FIG. 9, which concerns the test piece having the outer surface thinning, is extracted.

Figure 11:
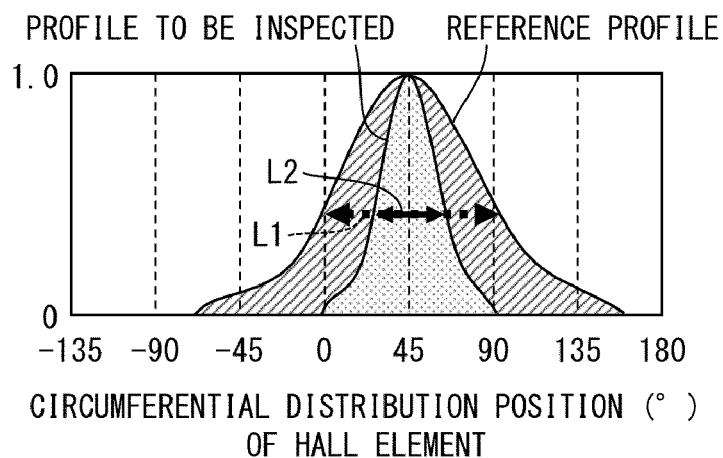

FIG. 11 is a view for describing a calculating method of calculating a thinned range by the second calculating method by the thinning measuring device in accordance with the embodiment of the present invention.

Figure 12:
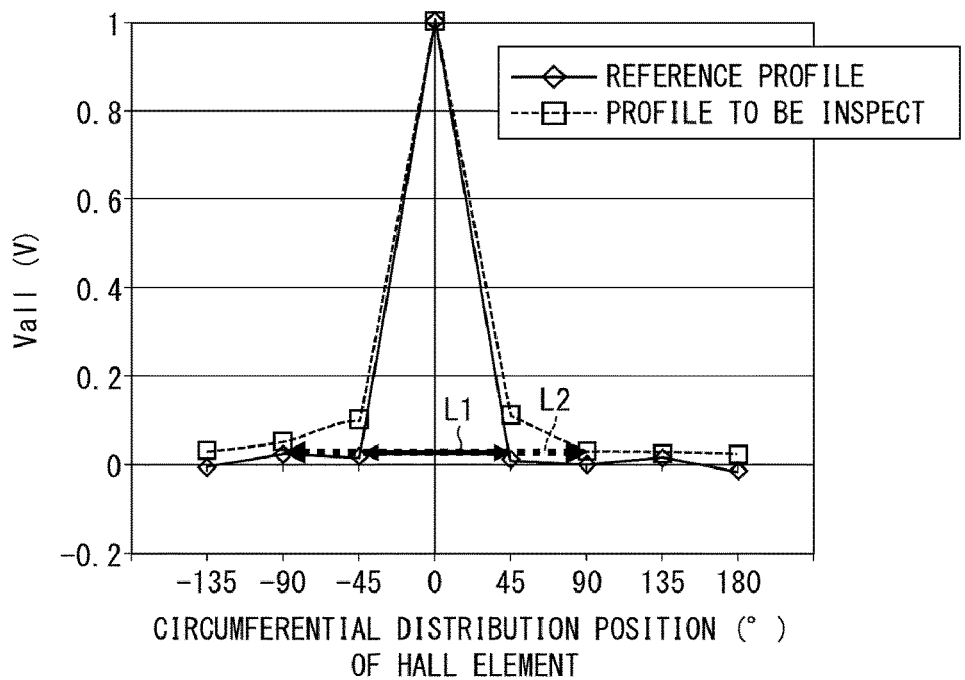

FIG. 12 is a view for describing a calculating method of calculating a thinned range by the second calculating method by the thinning measuring device in accordance with the embodiment of the present invention.

Figure 13:
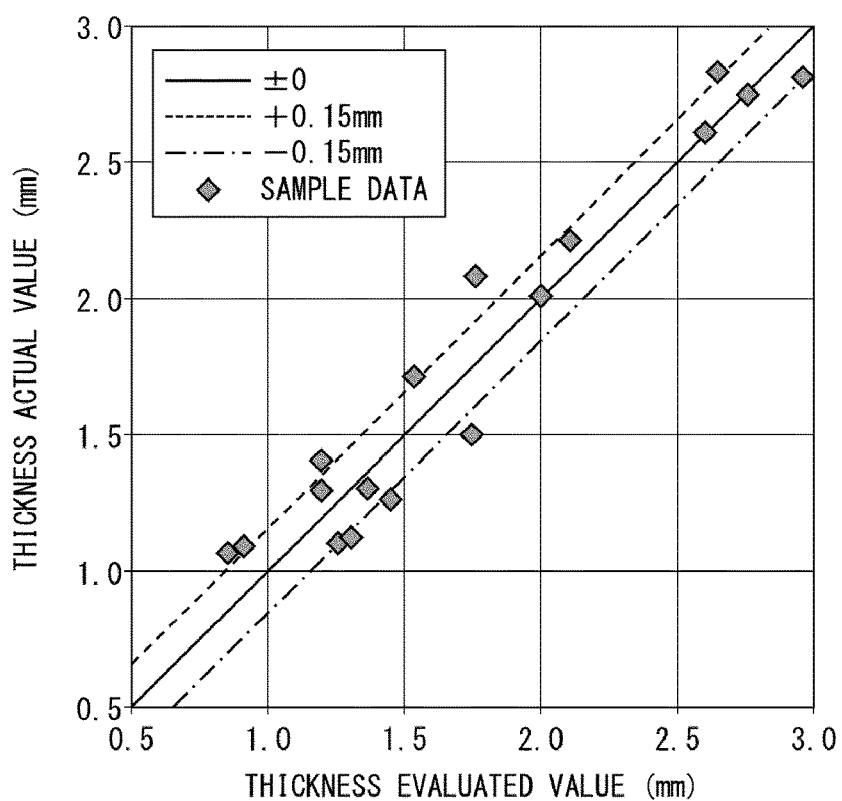

FIG. 13 is a graph showing relationships between (i) thickness evaluated values obtained by measuring pipes used in actual production models by the thinning measuring device in accordance with the embodiment of the present invention and (ii) thickness actual values obtained by actually measuring the pipes used in the actual production models.

Figure 14:
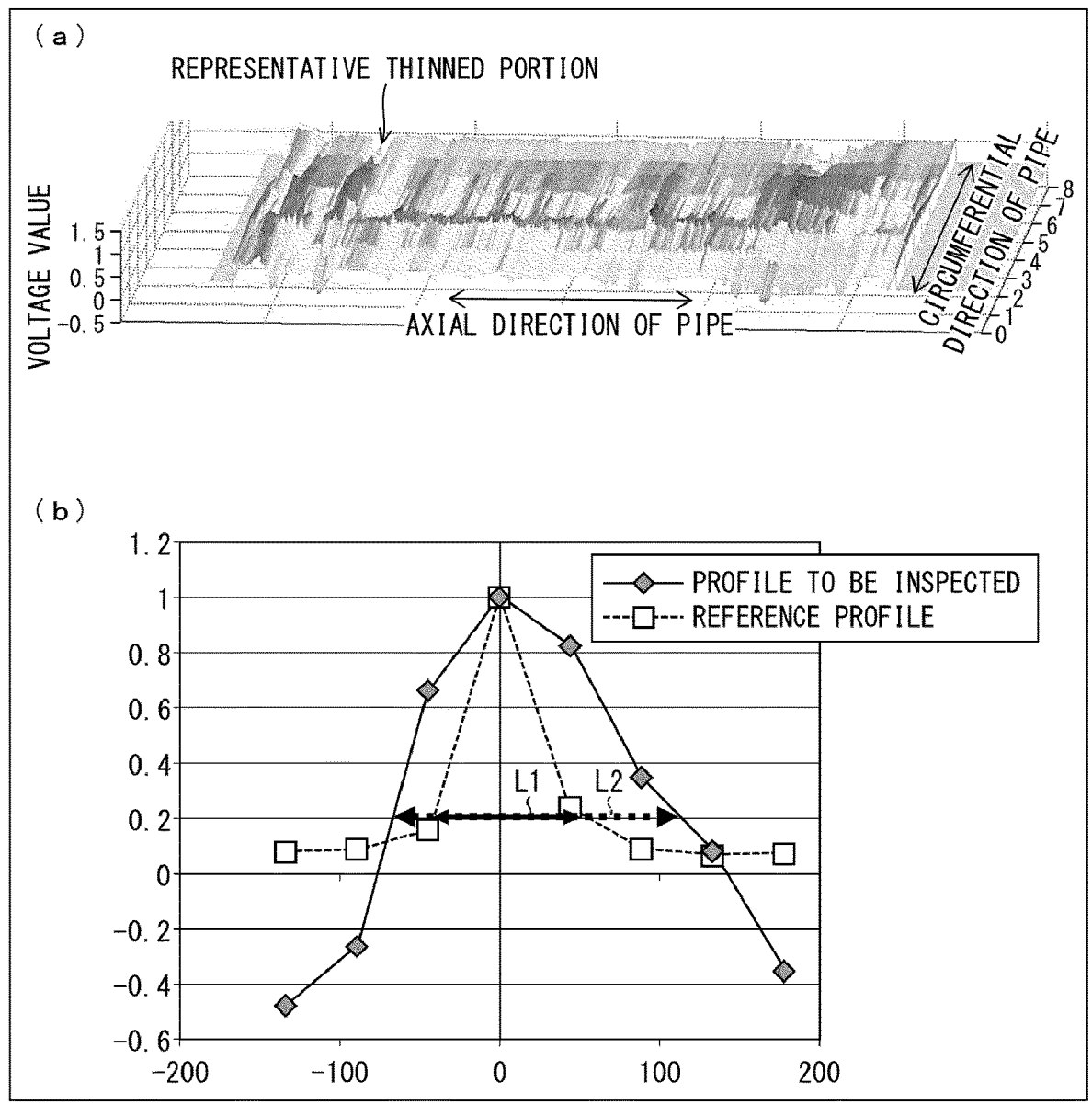

(a) of FIG. 14 is a graph plotting output voltages from Hall elements in a case where a magnetic pipe having inner surface thinning is inspected by the thinning measuring device in accordance with the embodiment of the present invention. (b) of FIG. 14 is a view for describing a calculating method of calculating a thinned range.

Figure 15:
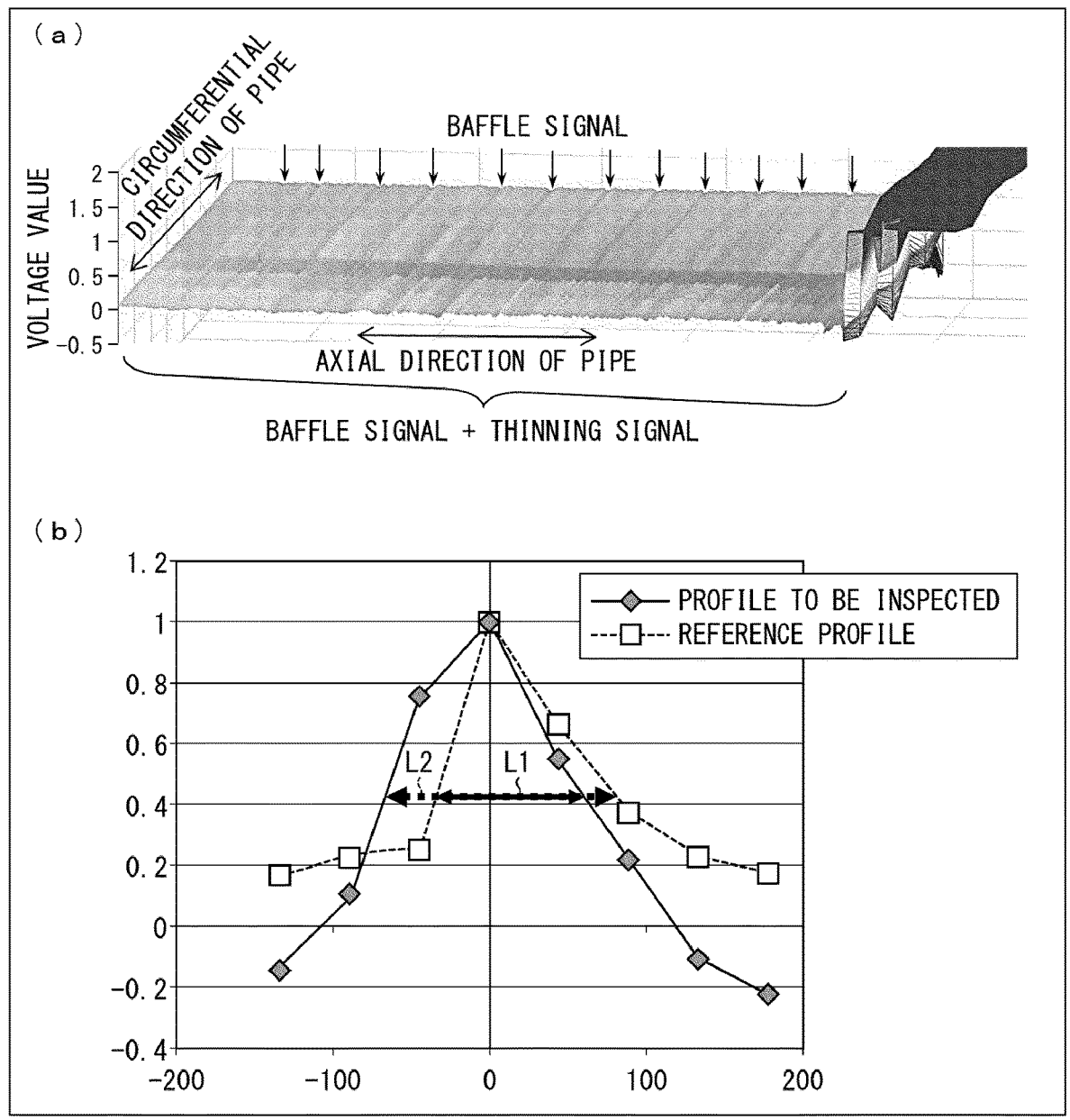

(a) of FIG. 15 is a graph plotting output voltages from Hall elements in a case where a magnetic pipe having outer surface thinning is inspected by the thinning measuring device in accordance with the embodiment of the present invention. (b) of FIG. 15 is a view for describing a calculating method of calculating a thinned range.

Figure 16:
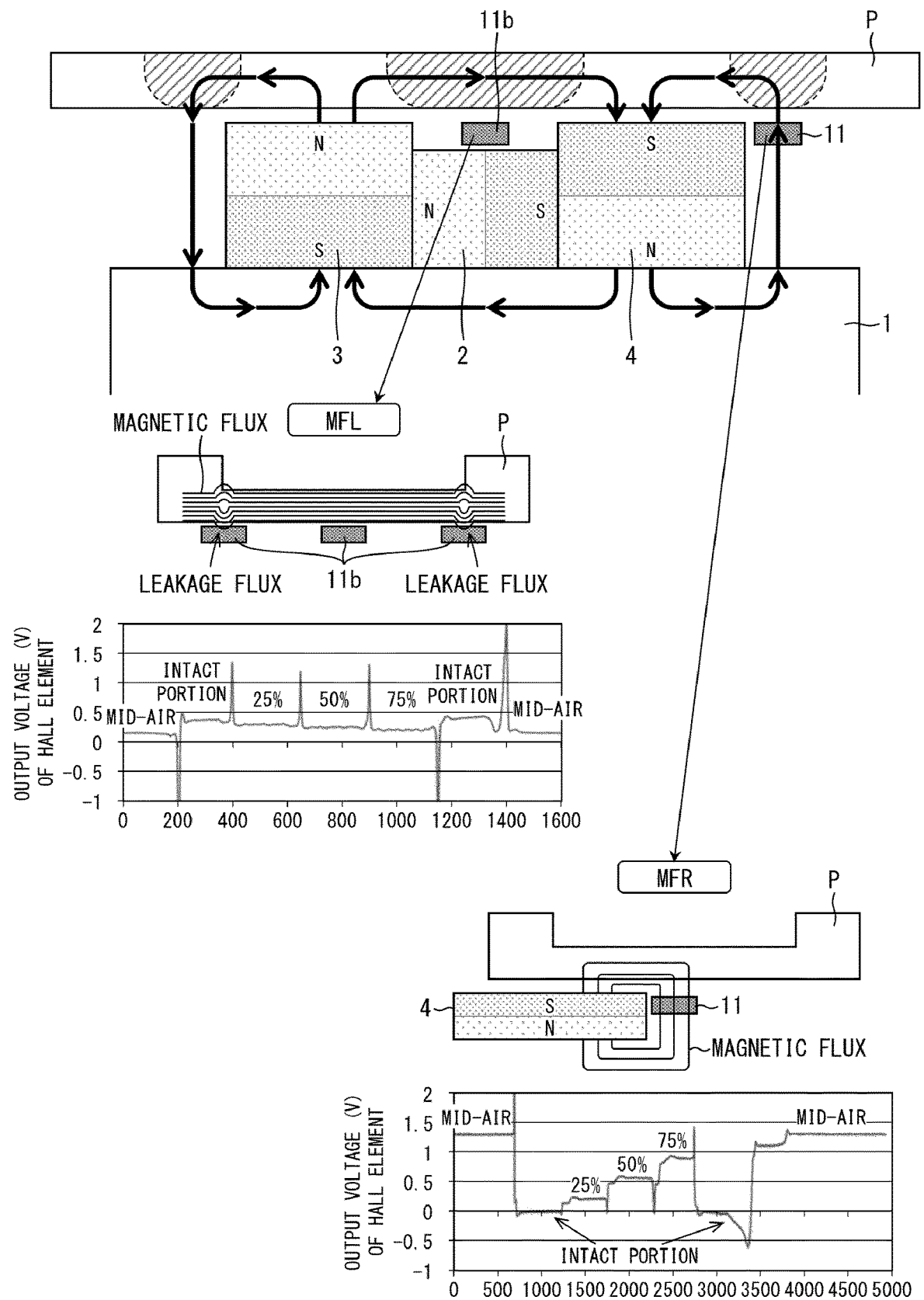

FIG. 16 is a view for describing a difference between a conventional magnetic flux leakage and the magnetic flux resistance used in an embodiment of the present invention.

DESCRIPTION OF EMBODIMENTS

A magnetic member is herein a member made of a magnetic material. Examples of the magnetic member encompass a cable, a wire, a plate-like member, and various structures, each of which is made of a magnetic material. Examples of a defect of the magnetic member encompass a thinned portion (hereinafter referred to as "thinning") and a crack. "Thinning" is a phenomenon in which a thickness of a member or the like is thinned by, for example, mechanical abrasion and/or chemical corrosion.

The following description will discuss an embodiment of the present invention. According to the present embodiment, thinning of a magnetic pipe, which serves as a magnetic member to be inspected, is inspected with use of (i) Hall elements serving as a magnetic sensor and (ii) an excitation and detection coil serving as an eddy current flaw sensor. However, the present invention is not limited to the present embodiment, and can be applied to more than a magnetic pipe and an inspection of thinning.

According to the present embodiment, the term "thinning measuring device" refers to a defect measuring device in accordance with an embodiment of the present invention. In discussing a defect in an embodiment of the present invention, (i) the term "outer surface thinning" refers to a front surface defect occurring to a front surface which is a counter surface facing an inspection probe and (ii) the term "inner surface thinning" refers to a back surface defect occurring to a back surface opposite the counter surface. The term "thinned range" refers to a defect range indicative of a range of a defect along a circumference of a cross section of a magnetic pipe in accordance with an embodiment of the present invention, which cross section is perpendicular to the axis of the magnetic pipe. The term "thinning range calculating section" refers to a defect range calculating section which calculates the defect range. The term "thinning depth" refers to a depth of a defect occurring to a magnetic pipe in accordance with an embodiment of the present invention. The term "defect depth calculating section" refers to a defect depth calculating section which calculates the depth of the defect. The term "thinned surface judging section" refers to a defect surface judging section which is capable of judging, based on a result of an eddy current test with use of an eddy current flaw sensor in accordance with an embodiment of the present invention, which of a front surface and a back surface of the magnetic member has a defect. The term "thinned surface judgment" refers to judging of whether a defect is (i) a front surface defect occurring to the front surface of the magnetic member, which front surface is a counter surface facing the inspection probe or (ii) a back surface defect occurring to the back surface of the magnetic member, which back surface is opposite the counter surface.

(1-1. Configuration of Inspection Probe 100)

Figure 1:
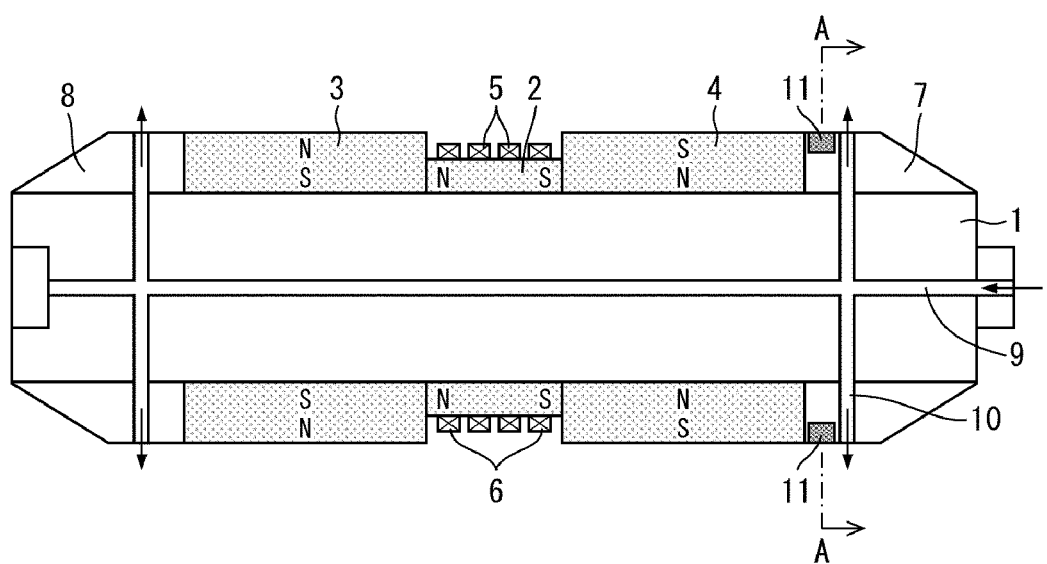
FIG. 1 is a cross-sectional view schematically illustrating an inspection probe for use in a thinning measuring device in accordance with an embodiment of the present invention.
Figure 2:
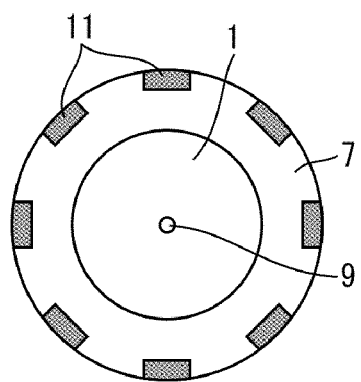
FIG. 2 is a cross-sectional view taken along the line A-A shown in FIG. 1.

FIG. 1 is a cross-sectional view schematically illustrating an inspection probe 100. FIG. 2 is a cross-sectional view taken along the line A-A shown in FIG. 1.

According to the present embodiment, a magnetic pipe is inspected by magnetization eddy current testing (magnetization ECT (Eddy Current Testing)) and the Magnetic Flux Resistance (MFR) through inserting the inspection probe 100 into the magnetic pipe and moving the inspection probe 100 in the magnetic pipe. Examples of the magnetic pipe to be inspected encompass pipes made of magnetic materials such as: carbon steel; ferritic stainless steel; and two-phase stainless steel having two phases which are a ferrite phase and an austenite phase.

As illustrated in FIG. 1, the inspection probe 100 includes a yoke 1, a first magnet 2, a second magnet 3, a third magnet 4, excitation and detection coils 5, eddy current control coils 6, guides 7 and 8, an air inlet port 9, air jetting ports 10, and Hall elements 11.

The yoke 1 is a hollow cylindrical member made of a magnetic material. Examples of the magnetic material of which the yoke 1 is made encompass high permeability metals such as carbon steel and low alloy steel.

The first magnet 2, the second magnet 3, and the third magnet 4 are attached to an outer peripheral surface of the yoke 1, and are provided in this order so as to form a Halbach array extending in axial directions of the yoke 1.

Specifically, the first magnet 2 is provided in a hollow cylindrical form which is made by a single magnet or obtained by combining a plurality of magnets into which a single magnet is divided along a circumference of the yoke 1. The first magnet 2 is mounted along an outer circumferential surface of a part of the yoke 1, which part is located at a center portion in the axial directions of the yoke 1 (i.e. the part sandwiched between the second magnet 3 and the third magnet 4). According to the present embodiment, the first magnet 2 is provided in a hollow cylindrical form, and is mounted on the yoke 1 so that an axis of the first magnet 2 is identical to an axis of the yoke 1. The first magnet 2 is polarized along a direction which is substantially parallel to the axial direction of the yoke 1, so that the first magnet 2 is magnetized such that (i) one magnetic pole of the first magnet 2, which magnetic pole faces the second magnet 3, is an N pole and (ii) the other magnetic pole, which magnetic pole faces the third magnet 4, is an S pole. Examples of the first magnet 2 encompass high-performance permanent magnets such as a neodymium magnet.

The second magnet 3 is mounted along an outer circumferential surface of the yoke 1, which outer circumferential surface is located toward axially one end with respect to the first magnet 2. According to the present embodiment, the second magnet 3 is (i) provided in a hollow cylindrical form which is made by a single magnet or obtained by combining a plurality of magnets into which a single magnet is divided along the circumference of the yoke 1 and (ii) mounted on the yoke 1 so that an axis of the second magnet 3 is identical to the axis of the yoke 1. The second magnet 3 is polarized in directions in which radii of the yoke 1 extend (i.e. polarized in directions facing a magnetic pipe P), so that the second magnet 3 is magnetized such that (i) one magnetic pole of the second magnet 3, which magnetic pole faces the yoke 1, is an S pole and (ii) the other magnetic pole (facing a magnetic pipe to be inspected) of the second magnet 3 is an N pole. Examples of the second magnet 3 encompass high-performance permanent magnets such as a neodymium magnet.

The third magnet 4 is mounted along an outer circumferential surface of the yoke 1, which outer circumferential surface is located toward axially the other end (i.e. located toward a side opposite from the side where the second magnet 3 is provided) with respect to the first magnet 2. According to the present embodiment, the third magnet 4 is (i) provided in a hollow cylindrical form which is made by a single magnet or obtained by combining a plurality of magnets into which a single magnet is divided along the circumference of the yoke 1 and (ii) mounted on the yoke 1 so that an axis of the third magnet 4 is identical to the axis of the yoke 1. The third magnet 4 is polarized in the directions in which the radii of the yoke 1 extend (i.e. polarized in directions facing a magnetic pipe P), so that the third magnet 4 is magnetized to have magnetic poles which are opposite those of the second magnet 3. Specifically, according to the present embodiment, the third magnet 4 is magnetized so that (i) the magnetic pole, which faces the yoke 1, is an N pole and (ii) the other magnetic pole is an S pole. Examples of the third magnet 4 encompass high-performance permanent magnets such as a neodymium magnet.

In a case where the first magnet 2 is thus mounted between the second magnet 3 and the third magnet 4 such that the magnetic pole facing the second magnet 3 and the magnetic pole facing the third magnet 4 are the N pole and the S pole, respectively (i.e. in a case where the second magnet 3, the first magnet 2, and the third magnet 4 are provided so as to form a Halbach array), it is possible to (i) cause an intensity (magnetic flux density) of a magnetic flux, which is formed by the second magnet 3 and the third magnet 4, to be high and (ii) cause a distribution of the magnetic flux to be uniform.

Note that the first magnet 2, the second magnet 3, and the third magnet 4 are not limited to any particular size, provided that these magnets can be inserted into a magnetic pipe to be inspected. However, the first magnet 2, the second magnet 3, and the third magnet 4 are to have sizes so that magnetic flux densities at respective end parts of the second magnet 3 and the third magnet 4, which end parts are located at axially outer parts of the yoke 1 (i.e. end parts further away from the first magnet 2), are each preferably 1.4 T to 2.4 T, and more preferably 1.5 T to 2.2 T. In a case where the magnetic flux densities each fall within the above ranges, a relative permeability of a magnetic pipe, which is to be inspected, changes linearly in response to a change in magnetic flux density. Therefore, by setting the magnetic flux densities to each fall within the above ranges, it is possible to carry out an inspection with higher accuracy by the magnetic flux resistance (MFR) described later.

The number of magnets to be provided is also not particularly limited. For example, it is possible to further provide another magnet between the first magnet 2 and the second magnet 3 and/or between the first magnet 2 and the third magnet 4. In such a case, it is also possible to provide magnets so that the magnets form a Halbach array.

A method by which to mount the first magnet 2, the second magnet 3, and the third magnet 4 on the yoke 1 is not limited to any particular one. For example, these magnets can be mounted on the yoke 1 with use of an adhesive or the like, or can be engaged with the yoke 1.

The excitation and detection coils 5 are wound along an outer circumferential surface of the first magnet 2 which is provided at the part of the yoke 1, which part is located at the center portion in the axial directions of the yoke 1. The excitation and detection coils 5 are intended for an eddy current test in which an eddy current flaw is inspected at a region of a magnetic pipe P, which region is magnetically saturated by the second magnet 3, the first magnet 2, and the third magnet 4 (or a region whose magnetic permeability is reduced enough to be sufficiently permeated with an eddy current). In an eddy current test, a thinning signal (detection signal) is detected when the excitation and detection coils 5 pass by a thinned portion of a magnetic pipe. A thinning signal correlates to (i) an amplitude corresponding to a thinning amount (volume) and (ii) a phase corresponding to a thinning depth. The excitation and detection coils 5 are not limited to any particular configuration, provided that a thinning signal can be detected. For example, the excitation and detection coils 5 can each be a coil obtained by winding, 10 times to 200 times, a copper wire having a wire diameter of 0.02 mm to 1.0 mm.

The eddy current control coils 6 are wound so as to sandwich, in directions extending along the axis of the yoke 1, the excitation and detection coils 5 which are provided around the outer circumferential surface of the first magnet 2. The eddy current control coils 6 excites an eddy current which flows in a direction opposite a direction in which an eddy current excited by the excitation and detection coils 5 flows. Since the eddy current control coils 6 are provided, an excess conductive range, which is excited by the excitation and detection coils 5, can be offset by an eddy current which is excited by the eddy current control coils 6 so as to flow in the opposite direction. This makes it possible to restrict an excess conductive range of an eddy current.

Note that FIG. 1 omits (i) conducting wires of the excitation and detection coils 5 and the eddy current control coils 6 and (ii) drawing ports for the conducting wires.

Figure 3:
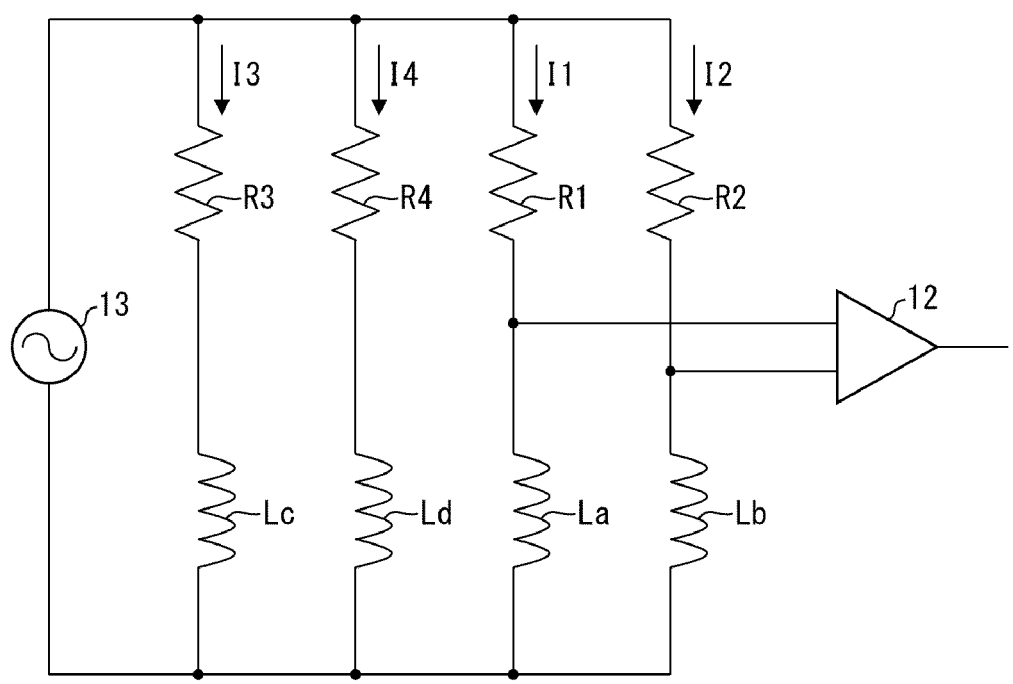
FIG. 3 is a circuit diagram illustrating an eddy current flaw detecting section of the inspection probe illustrated in FIG. 1.

FIG. 3 is a circuit diagram illustrating an eddy current flaw detecting section of the inspection probe 100. As illustrated in FIG. 3, two excitation and detection coils 5 (La, Lb), two eddy current control coils 6 (Lc, Ld), and four variable resistors R1, R2, R3, and R4 are connected in parallel between a power supply 13 and an eddy current flaw detector 12. The detection coils La and Lb and the variable resistors R1 and R2 are connected to signal input terminals of the eddy current flaw detector 12 so that the detection coils La and Lb and the variable resistors R1 and R2 form a Wheatstone bridge circuit.

An output terminal of the eddy current flaw detector 12 is connected, via a conducting wire, to an eddy current flaw detecting section 30 described later.

An eddy current test is carried out as follows: First, respective impedances of the excitation and detection coils 5 and of the eddy current control coils 6 at a certain test frequency (e.g. 100 kHz) and at a certain voltage applied (e.g. 5 V) are measured. Then, resistances of the variable resistors R1 and R2 are adjusted to the impedances thus measured. In so doing, a combined impedance of the excitation and detection coils 5 and the variable resistors R1 and R2 in combination is measured, a flaw detection is carried out while the resistances of the variable resistors R3 and R4 to be connected to the eddy current control coils 6 are changed around the combined impedance thus measured. Finally, a flaw detection is carried out under a condition in which detectability is good. A speed of a flaw detection by the inspection probe 100 is set to, for example, approximately 2 mm/sec to 50 mm/sec. In a case where a smaller amount of thinning needs to be accurately detected, the speed is set to approximately 2 mm/sec to 10 mm/sec.

As illustrated in FIGS. 1 and 2, eight Hall elements 11 are provided at substantially regular intervals along the circumference of the yoke 1 in the vicinity of the end part of the third magnet 4, which end part is located further away from the first magnet 2). These Hall elements 11 each supply, to a magnetic flux resistance flaw detecting section 40 described later, a voltage value (output signal) corresponding to a density (intensity) of a magnetic flux passing through the third magnet 4 and a magnetic pipe. Specifically, each of the Hall elements 11, which is provided on a magnetic circuit formed by the third magnet 4 and a magnetic pipe P, (i) detects a density of a magnetic flux flowing through the magnetic circuit and then (ii) supplies, to the magnetic flux resistance flaw detecting section 40, an output signal corresponding to the results of the detection. With use of the output signal from each of the Hall elements 11, the magnetic flux resistance flaw detecting section 40 quantitatively evaluates thinning by a magnetic flux resistance described later. FIG. 1 omits conducting wires of the Hall elements 11 and (ii) drawing ports for the conducting wires.

According to the present embodiment, the eight Hall elements 11 are provided along the circumference of the yoke 1. However, the number of Hall elements 11 is not limited to eight. According to the present embodiment, the Hall elements serve as a magnetic sensor. However, the type of the magnetic sensor is not limited to any particular one, provided that it is possible to output an output signal which corresponds to a magnetic flux density. In addition, a position at which to the provide the Hall elements 11 can be any position, provided that it is possible to measure a density of a magnetic flux passing through the third magnet 4 and a magnetic pipe P. For example, the Hall elements 11 can be provided so as to face the third magnet 4 with respect to the axis of the inspection probe 100 or with respect to a circumference of the inspection probe 100. Furthermore, the position at which to provide the Hall elements 11 can be such that the hall elements 11 are (i) in contact with the third magnet 4 or (ii) spaced from the third magnet 4.

According to the present embodiment, a density of a magnetic flux passing through the third magnet 4 and a magnetic pipe P is measured by the hall elements 11. However, the present invention is not limited to this configuration. For example, it is possible to (i) provide Hall elements 11 on a magnetic circuit formed by the second magnet 3 and a magnetic pipe P and (ii) cause the Hall elements 11 to measure a density of a magnetic flux passing through the second magnet 3 and the magnetic pipe P. Alternatively, it is also possible to (i) provide Hall elements 11 on a magnetic circuit formed by the second magnet 3 and a magnetic pipe P and provide other Hall elements 11 on a magnetic circuit formed by the third magnet 4 and the magnetic pipe P and (ii) cause the Hall elements 11 and the other Hall elements 11 to respectively measure a density of a magnetic flux passing through the third magnet 4 and the magnetic pipe P and a density of a magnetic flux passing through the second magnet 3 and the magnetic pipe P.

The guides 7 and 8 are provided at respective axially end parts of the inspection probe 100. The guides 7 and 8 are made of, for example, acetal resin or stainless steel. The guides 7 and 8 are mounted on the yoke 1 by a screw structure.

The air inlet port 9 is provided through substantially center parts of the yoke 1, which substantially center parts are located at respective axially end surfaces of the yoke 1. The plurality of air jetting ports 10 are provided in the vicinity of the end parts of the yoke 1 so as to (i) be connected to the air inlet port 9 and (ii) extend in the directions in which the radii of the yoke 1 extend. This causes air to be (i) introduced through the air inlet port 9 which is provided through both the end surfaces of the yoke 1 and (ii) jetted from the air jetting ports 10. In a detection of a flaw of a magnetic pipe, it is difficult to scan (move) and center an inspection probe 100 due to the inspection probe 100 being attached to an inner surface of the magnetic pipe by a strong permanent magnet mounted on the inspection probe 100. However, in a case where air is jetted from the air jetting ports 10 in a direction substantially perpendicular to a counter surface of a magnetic pipe which counter surface facing the inspection probe 100, it is possible to reduce the attachment to the pipe so as to make it easy to scan the inspection probe 100. Note that the air jetting ports 10 has a pore size of, for example, approximately 2 mmφ, and approximately 6 to 10 of the air jetting ports 10 are to be provided so along the circumference of the yoke 1 as to extend from the air inlet port 9.

(1-2. Overview of Magnetic Flux Resistance)

FIG. 16 is a view for describing a difference between a conventional magnetic flux leakage (MFL) and the magnetic flux resistance (MFR) used in the present embodiment.

According to the magnetic flux leakage, as illustrated in FIG. 16, (i) a second magnet 3, a first magnet 2, and a third magnet 4 are provided in this order to form a Halbach array, (ii) a Hall element 11b is provided on a counter surface of the first magnet 2, which counter surface faces a magnetic pipe P, and (iii) the Hall element 11b detects that a magnetic flux, which flows in the magnetic pipe P, is leaking out at a thinned portion of the magnetic pipe P. In this case, leakage flux occurs only at portions where the shape of the magnetic pipe is discontinuous, such as a thinned end part, and, as illustrated in FIG. 16, leakage flux does not occur at (i) portions where thinning is occurring over an entire surface or (ii) thinning is occurring gradually. Therefore, according to the magnetic flux leakage, it is not possible to detect thinning over an entire surface, detect a gradually thinned portion, or quantitatively evaluate thinning.

In contrast, according to the magnetic flux resistance, (i) the Hall elements 11 are provided on a magnetic circuit formed by (a) a magnet (e.g. the third magnet 4 polarized in directions facing a magnetic pipe P) provided at an end part of a Halbach array and (b) a magnetic pipe P and (ii) a density of a magnetic flux flowing through the magnet and the magnetic pipe P is measured. This makes it possible to directly measure a magnetic flux density which increase/decreases depending on a thickness of the magnetic pipe P. Therefore, according to the magnetic flux resistance, it is possible to (i) detect thinning over an entire surface and a gradually thinned portion and (ii) accurately measure a thinning depth and the thickness of the magnetic pipe P.

(1-3. Configuration of Thinning Judging Section 20)

Figure 4:
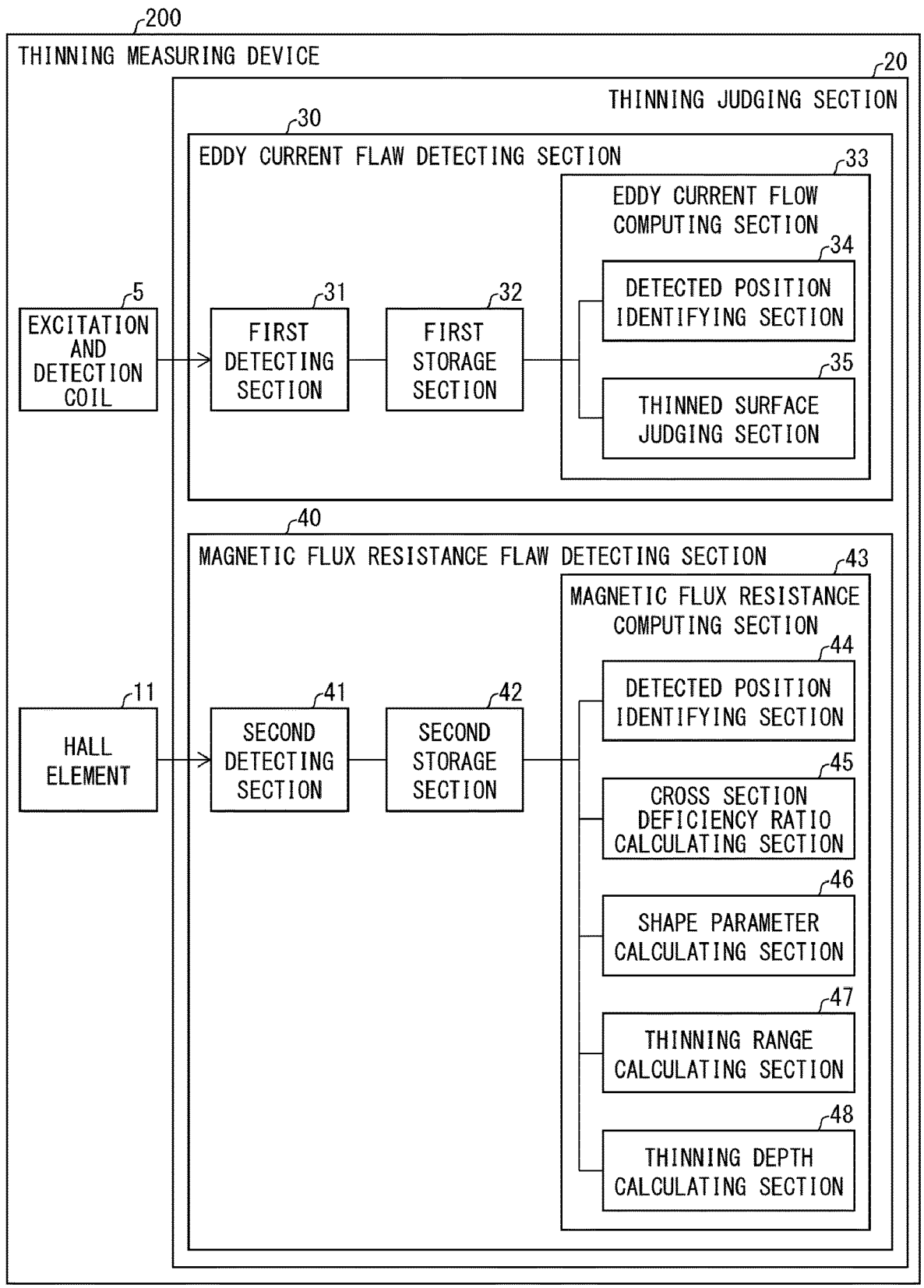
FIG. 4 is a block diagram illustrating a configuration of a thinning judging section included in the thinning measuring device in accordance with the embodiment of the present invention.
Figure 5:
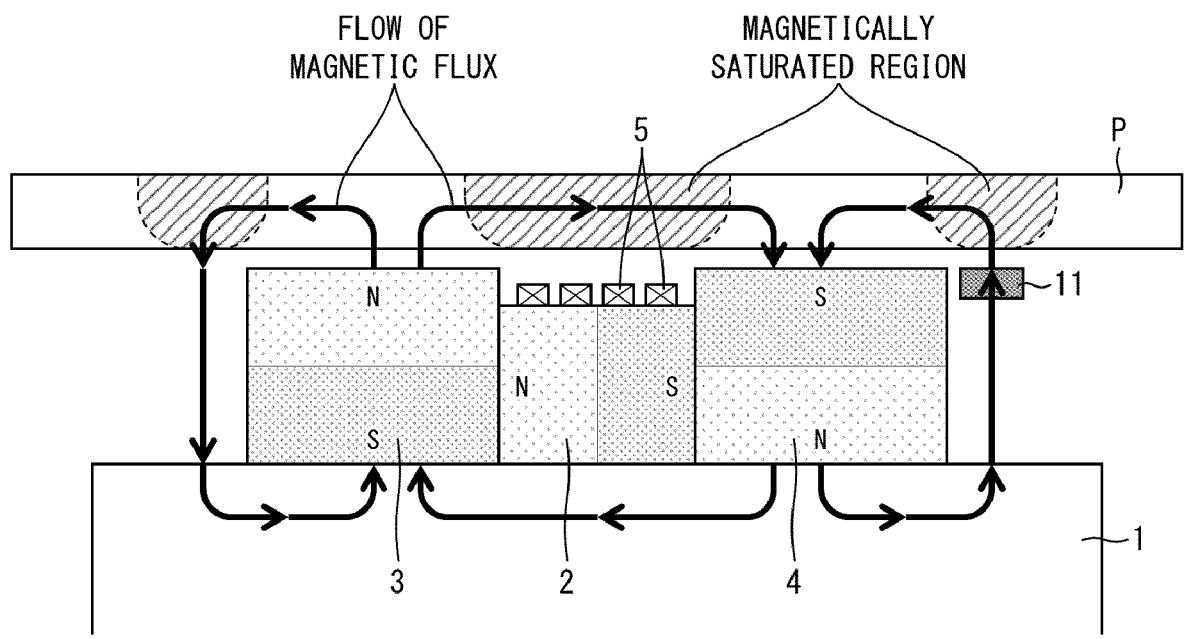
FIG. 5 is a view for schematically describing a thinning judging process carried out by the thinning measuring device in accordance with the embodiment of the present invention.

FIG. 4 is a block diagram illustrating a configuration of a thinning measuring device 200 in accordance with the present embodiment. FIG. 5 is a view for describing an overview of a thinning judging process in accordance with the present embodiment.

As illustrated in FIG. 4, the thinning measuring device 200 includes the excitation and detection coils 5, the Hall elements 11, and a thinning judging section 20. The thinning judging section 20 includes the eddy current flaw detecting section 30 and the magnetic flux resistance flaw detecting section 40.

According to the present embodiment, as illustrated in FIGS. 4 and 5, an eddy current test is carried out with use of the excitation and detection coils 5, and then the eddy current flaw detecting section 30 judges, with use of a detection signal obtained from the eddy current test, whether thinning is occurring to an inner surface or an outer surface of a magnetic pipe P. In addition, a density of a magnetic flux flowing through the third magnet 4 and the magnetic pipe P is detected with use of the Hall elements 11. Then, with use of a result of the detection by the eddy current flaw detecting section 30 and a result of the judging of a thinned surface, the magnetic flux resistance flaw detecting section 40 quantitatively evaluates the thinning of the magnetic pipe P. According to the present embodiment, the inner surface of the magnetic pipe P refers to a front surface which is counter surface facing the inspection probe 100, and the outer surface refers to a back surface opposite from the counter surface.

As illustrated in FIG. 4, the eddy current flaw detecting section 30 includes a first detecting section 31, a first storage section 32, and an eddy current flow computing section 33. The eddy current flow computing section 33 includes a detected position identifying section 34 and a thinned surface judging section 35.

The magnetic flux resistance flaw detecting section 40 includes a second detecting section 41, a second storage section 42, and a magnetic flux resistance computing section 43. The magnetic flux resistance computing section 43 includes a detected position identifying section 44, a cross section deficiency ratio calculating section 45, a shape parameter calculating section 46, a thinned range calculating section 47, and a thinning depth calculating section 48.

The first detecting section 31 obtains a detection signal which is supplied from the excitation and detection coils 5 via the eddy current flaw detector 12. Then, the first detecting section 31 controls the first storage section 32 to store the detection signal and detected time (detected timing) at which the detection signal was obtained such that the detection signal and the detected time are associated with each other.

The second detecting section 41 obtains respective output voltage values of the Hall elements 11, and then controls the second storage section 42 to store the output voltage values and corresponding detected times (detected timings) such that the output voltage values and the corresponding detected times are associated with each other.

Configurations of the first storage section 32 and the second storage section 42 are not particularly limited. Examples of each of the first storage section 32 and the second storage section 42 encompass storage media such as (i) tapes such as a magnetic tape and a cassette tape, (ii) disks including magnetic disks such as a floppy disk (Registered Trademark) and a hard disk and optical disks such as a CD-ROM, an MO, an MD, a DVD, and a CD-R, (iii) cards such as an IC card (including a memory card) and an optical card, and (iv) semiconductor memories such as a mask ROM, an EPROM, an EEPROM (Registered Trademark), and a flash ROM.

Based on the detection signals which have been supplied from the excitation and detection coils 5 and stored in the first storage section 32 and on the corresponding detected times and based on the output voltage values which have been supplied from the Hall elements 11 and stored in the second storage section 42 and on the corresponding detected times, the detected position identifying section 34 and the detected position identifying section 44 associate the following with each other: (i) detected positions of the magnetic pipe P, which detected positions correspond to the detection signals from the excitation and detection coils 5 and (ii) detected positions of the magnetic pipe P, which detected positions correspond to the output voltage values from the Hall elements 11.

Based on the detection signals from the excitation and detection coils 5, the thinned surface judging section 35 judges whether thinning that is present in the magnetic pipe to be inspected is inner surface thinning or outer surface thinning.

Based on a cross section deficiency ratio calculating formula (described later), the cross section deficiency ratio calculating section 45 calculates a cross section deficiency ratio at positions of the magnetic pipe along the axis of the magnetic pipe. The "cross section deficiency ratio" refers to a ratio of an area of a deficient portion to an area of an entire portion of a cross section perpendicular to the axis of the magnetic pipe. The "cross sectional area of a deficient cross section" refers to a cross sectional area which has been reduced by thinning. According to the present embodiment, different cross section deficiency ratio calculating formulas are used, depending on whether thinning is of an inner surface or of an outer surface (described later).

Based on the output voltage values from the Hall elements 11, the shape parameter calculating section 46 calculates shape parameters. According to the present embodiment, the shape parameters calculated by the shape parameter calculating section 46 are (i) Vmax which is a maximum value of the output voltage values from the Hall elements 11 and (ii) Vall which is a combined value obtained by combining values which are obtained normalizing (dividing), by Vmax, each of the output voltage values from the Hall elements 11.

Based on the output voltage values from the Hall elements 11, the thinned range calculating section 47 calculates a thinned range of the magnetic pipe.

Based on the cross section deficiency ratio calculated by the cross section deficiency ratio calculating section 45 and on the thinned range calculated by the thinned range calculating section 47, the thinning depth calculating section 48 calculates a thinning depth in radial directions of the magnetic pipe.

Note that the eddy current flow computing section 33 and the magnetic flux resistance calculating section 43 can be each an integrated circuit (hardware logic) such as an ASIC (application specific integrated circuit), or can be each achieved by a computer executing software, which computer includes a processor such as a CPU. Alternatively, the eddy current flow computing section 33 and the magnetic flux resistance calculating section 43 can each be achieved by a combination of such an integrated circuit and software execution of such a computer.

Furthermore, the eddy current flow computing section 33 and the magnetic flux resistance calculating section 43 can be included in a housing in which the first detecting section 31, the first storage section 32, the second detecting section 41, and the second storage section 42 are included, or can be provided separately from the first detecting section 31, the first storage section 32, the second detecting section 41, and the second storage section 42. In the latter case, the eddy current flow computing section 33 and the magnetic flux resistance calculating section 43 (i) obtain respective pieces of information, which are stored in the first storage section 32 and the second storage section 42, respectively, via, for example, wired communications, wireless communications, or a storage medium which can be attached and detached and then (ii) carry out respective computing processes.

(1-4. Thinning Inspection Process)

Figure 6:
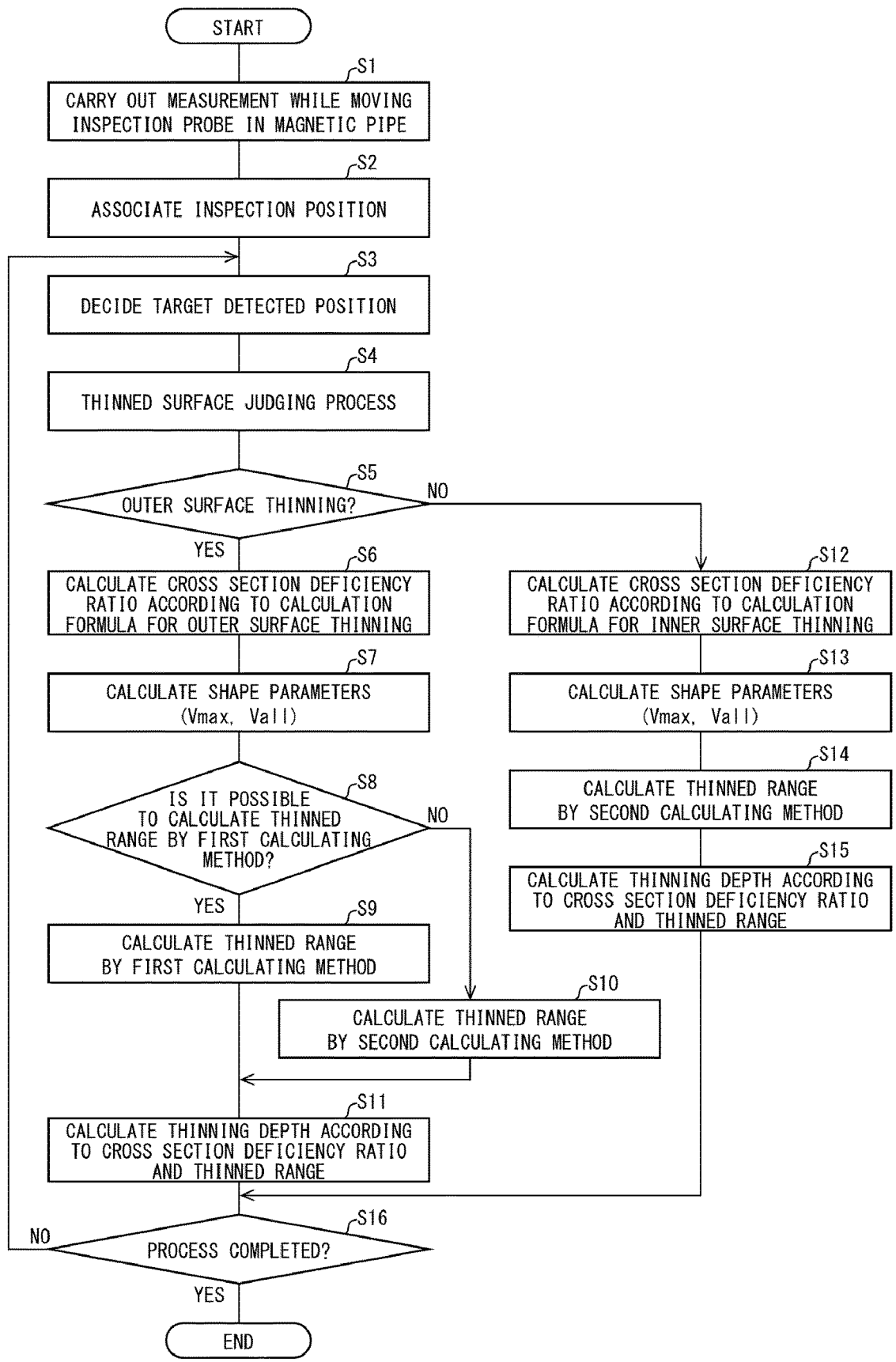
FIG. 6 is a flow chart illustrating a flow of a process carried out by the thinning measuring device in accordance with the embodiment of the present invention.

FIG. 6 is a flow chart illustrating a flow of a thinning inspection process according to the present embodiment.

First, the inspection probe 100 is inserted into a magnetic pipe to be inspected, and measurement is carried out with use of the excitation and detection coils 5 and the Hall elements 11 while the inspection probe 100 is being moved axially in the magnetic pipe (S1).

Specifically, the first detecting section 31 obtains (i) detection signals supplied from the excitation and detection coils 5 via the eddy current flaw detector 12 and (ii) detected times at which the respective detection signals were obtained. Then, the first detecting section 31 controls the first storage section 32 to store the detection signals and the detected times such that the detection signals and the corresponding detected times are associated with each other. In addition, the second detecting section 41 obtains (i) output voltage values from the Hall elements 11 and (ii) detected times at which the respective output voltage values were obtained. Then, the second detecting section 41 controls the second storage section 42 to store the output voltage values and the detected times such that the output voltage values and the corresponding detected times are associated with each other.

Note that a method in which the inspection probe 100 is moved in a magnetic pipe is not limited to any particular one. For example, the inspection probe 100 can be moved by (i) pulling the inspection probe 100 with use of a wire or the like which is connected to the inspection probe 100 or (ii) pushing the inspection probe 100 with use of a bar-like member. Alternatively, the inspection probe 100 can move by itself with use of a driving section provided on the inspection probe 100.

Next, based on the information stored in the first storage section 32, the detected position identifying sections 34 and 44 associate the following with each other: (i) detected positions (positions along the axial direction of the magnetic pipe) corresponding to the detection signals from the excitation and detection coils 5 and (ii) detected positions (positions along the axial direction of the magnetic pipe) corresponding to the output voltage values from the Hall elements 11 (S2).

Next, the thinned surface judging section 35 extracts, as a target detected position, one of the detected positions associated in the step S2 (S3), and then carries out a thinned surface judging process with respect to the target detected position (i.e. process of judging whether thinning at the target detected position is outer surface thinning or inner surface thinning) (S4). In this way, according to the present embodiment, (i) in a case where the thinning is outer surface thinning, a quantitative evaluation of the thinning (calculation of a cross section deficiency ratio, a thinned range, and a thinning depth) is carried out with use of an evaluation algorithm (S5 through S11) intended for outer surface thinning and (ii) in a case where the thinning is inner surface thinning, a quantitative evaluation of the thinning is carried out with use of an evaluation algorithm (S12 through S15) intended for inner surface thinning.

According to measurement results of magnetization eddy current testing, a phase angle of an output voltage value largely varies, depending on whether thinning is present on an inner surface side of a magnetic pipe or the thinning is present on an outer surface side of the magnetic pipe. Specifically, according to magnetization eddy current testing, a graph, in which an X-axis and a Y-axis respectively represent an X-direction voltage amplitude and a Y-direction voltage amplitude, shows that (i) in a case where thinning is present on an inner surface side, detection results tend to fall in a first quadrant and (ii) in a case where thinning is present on an outer surface, detection results tend to fall in a third quadrant. Therefore, by using the magnetization eddy current testing, it is possible to easily judge whether thinning is present on an inner surface side of a magnetic pipe or is present on an outer surface side of the magnetic pipe.

According to the present embodiment, a thinned surface (whether thinning is present on an outer surface side of a magnetic pipe or is present on an inner surface side of the magnetic pipe) is judged by the magnetization eddy current testing. This makes it possible to judge a thinned surface in real time by, with use of an inspection probe 100, simultaneously obtaining (i) measurement data by a magnetic flux resistance and (ii) measurement data by the magnetization eddy current testing. In a case where, for example, inner surface thinning and outer surface thinning are both present, it is particularly advantageous to judge thinned surfaces by the magnetization eddy current testing. Note, however, that a method of judging a thinned surface is not limited to the magnetization eddy current testing, and thinned surface can be judged by use of other judging methods. Alternatively, a user can judge a thinned surface in a case where it is possible to identify the thinned surface by, for example, (i) an environment in which a magnetic pipe to be inspected is used and/or (ii) results of visual inspection.

Next, based on the results of the judgment by the thinned surface judging section 35, the cross section deficiency ratio calculating section 45 judges whether or not thinning at a target detected position is outer surface thinning (S5).

In a case where it is judged in the step S5 that the thinning is outer surface thinning, the cross section deficiency ratio calculating section 45 calculates a cross section deficiency ratio Cout according to a cross section deficiency ratio calculating formula for outer surface thinning (S6).

Note that a cross section deficiency ratio calculating formula for outer surface thinning and a cross section deficiency ratio calculating formula for inner surface thinning are set in advance, based on results of measuring, by a magnetic flux resistance with use of an inspection probe 100, test pieces (test magnetic pipes) each having a plurality of types of thinning.

(a) of FIG. 7 is a view for describing an example of test pieces having a plurality of pieces of outer surface thinning. (b) of FIG. 7 is a view for describing examples of test pieces having a plurality of pieces of inner surface thinning.

As illustrated in (a) of FIG. 7, the test piece, which had the outer surface thinning and was used, had 9 types of thinning in an STB pipe having an outer diameter of 25.4 mm and a thickness of 2.0 mm, the 9 types of thinning differing in terms of thinned range and thinning rate. That is, 9 types of thinning of [thinned range, thinning rate] of the test piece were [45°, 25%], [45°, 50%], [45°, 75%], [90°, 25%], [90°, 50%], [90°, 75%], [135°, 25%], [135°, 50%], and [135°, 75%]. For example, a thinned range of 360° indicates that thinning is occurring over an entire circumference of the magnetic pipe P. Note that "thinning rate" according to the present embodiment is a value of a ratio of a thickness of a magnetic pipe P which is intact to a depth of a thinned portion extending in directions in which the magnetic pipe P and the first magnet 2 face each other. For example, in a case where the thinning rate of a magnetic pipe P is 75%, the thickness of the magnetic pipe P is ¼ of that of the magnetic pipe P which is intact. Note also that each of the pieces of thinning had a width of 5 mm, which width extends along an axis of the magnetic pipe.

As illustrated in (b) of FIG. 7, the test pieces having inner surface thinning were: (i) a test piece having, in an STB pipe having an outer diameter of 25.4 mm and a thickness of 2.0 mm, (A) thinning having a form of a flat-bottomed hole and having a diameter of 5 mm and a thinning rate of 25% and (B) thinning having a form of a flat-bottomed hole and having a diameter of 5 mm and a thinning rate of 50% and (ii) a test piece having, in an STB pipe having an outer diameter of 25.4 mm and a thickness of 2.0 mm, (A) thinning having a thinned range of 90°, a thinning rate of 25%, and a width of 5 mm which extends along the axis of the magnetic pipe and (B) thinning having a thinned range of 90°, a thinning rate of 50%, and a width of 5 mm which extends along the axis of the magnetic pipe.

c) of FIG. 7 is a graph showing relationships between (i) the results of measuring, by a magnetic flux resistance, the test pieces illustrated in (a) and (b) of FIG. 7 (i.e. combined value V_sum(V) obtained by combining the output voltage values from the respective Hall elements 11) and (ii) corresponding ones of actual cross section deficiency ratios of the thinning of the respective test pieces (i.e. cross section deficiency ratios calculated based on actual values). The actual values were measured by use of an ultrasonic thickness meter or a submersion rotary ultrasonic thickness measuring method. Note that this graph also plots the results of measuring (i) entire circumferential groove thinning on the outer surface (outer surface circumferential groove thinning) and (ii) entire circumferential groove thinning on the inner surface (inner surface circumferential groove thinning).

As illustrated in (c) of FIG. 7, in both cases of local thinning and entire circumferential groove thinning, there are extremely high correlations between the combined values V_sum of the output voltage values from the Hall elements 11 and the corresponding cross section deficiency ratios, so that the relationships can be approximated by a linear function.

Therefore, according to the present embodiment, a cross section deficiency ratio calculating formula for calculating a cross section deficiency ratio from V_sum is calculated in advance based on relationships between (i) V_sum based on the results of measuring test pieces prepared in advance and (ii) actual cross section deficiency ratios.

Note that as illustrated in (c) of FIG. 7, the graph of V_sum and the cross section deficiency ratios shows that although the cross section deficiency ratio calculating formula for outer surface thinning and the cross section deficiency ratio calculating formula for inner surface thinning result in substantially identical slopes, a value of an intercept according to the cross section deficiency ratio calculating formula for inner surface thinning is smaller.

Specifically, while the cross section deficiency ratio calculating formula for calculating a cross section deficiency ratio Cout for outer surface thinning is represented by "Cout=a×V_sum", the cross section deficiency ratio calculating formula for calculating a cross section deficiency ratio Cin for inner surface thinning is represented by "Cin=a×V_sum-b". Note that respective values of a and b are decided, prior to a thinning inspection process of a magnetic pipe to be measured, by measuring a test piece which is prepared in advance according to a material, a size, and the like of a magnetic pipe to be measured.

After the cross section deficiency ratio Cout of outer surface thinning is calculated in the step S6, the shape parameter calculating section 46 calculates certain shape parameters based on the output voltage values from the Hall elements 11 (S7).

According to the present embodiment, the shape parameters to be calculated are (i) Vmax which is a maximum value of the output voltage values from the Hall elements 11 and (ii) Vall which is a combined value obtained by combining values which are obtained normalizing, by Vmax, each of the output voltage values from the Hall elements 11.

FIG. 8 is a view for describing an example of output voltage values from eight Hall elements 11 (ch1 to ch8) in a case where flaw detection of thinning over an entire surface and of local thinning is carried out. As illustrated in FIG. 8, in a case of thinning over an entire surface where output voltage values from all of the Hall elements 11 are substantially identical, the output voltage values are distributed so as to form a rectangle. On the other hand, in a case of local thinning, an output voltage value of a Hall element 11 provided directly under a portion where the local thinning is occurring becomes a highest value. In this case, the output voltage values are distributed so as to form a mountain-like shape where the output voltage values that are further from the highest output voltage value are lower.

Next, the thinned range calculating section 47 judges whether or not a thinned range can be calculated by a certain first calculating method in which the shape parameters (Vmax, Vall) calculated by the shape parameter calculating section 46 are used (S8). Note that a judging method in the step S8 will be described later.

In a case where it is judged in the step S8 that the thinned range can be calculated by the first calculating method, the thinned range calculating section 47 calculates a thinned range by the first calculating method (S9). In a case where it is judged that the thinned range cannot be calculated by the first calculating method, the thinned range calculating section 47 calculates a thinned range by a certain second calculating method (S10).

FIG. 9 is a graph plotting Vall and Vmax along a horizontal axis and a vertical axis, respectively, which Vall and Vmax are calculated based on the results of flaw detection of (i) the above-described test piece having the outer surface thinning (see (a) of FIG. 7) and (ii) the above-described test piece having the inner surface thinning (see (b) of FIG. 7). FIG. 10 is a graph in which data, of all of pieces of data shown in FIG. 9, which concerns the test piece having the outer surface thinning, is extracted.

As illustrated in FIGS. 9 and 10, in a case where Vall is a certain value (e.g. 3V) or more, output voltage values in the case of outer surface thinning are, in a graph plotting Vall and Vmax, clearly distributed so as to correspond to a thinned range along the circumference. Therefore, (i) functions (data for calculating a thinned range), which show correlations between Vall and Vmax for respective thinned ranges, are calculated according to the results of flaw detection of test pieces having outer surface thinning and (ii) interpolation calculation with use of the functions is carried out. This makes it possible to calculate a thinned range corresponding to Vall and Vmax which are obtained by flaw detection of a magnetic pipe to be inspected. In the present embodiment, this calculating method is referred to as "first calculating method".

Specifically, in the first calculating method, the following straight lines are calculated in advance according to the results of flaw detection of test pieces having outer surface thinning: (i) a straight line L45 indicative of a correlation between Vall and Vmax in a case where a thinned range is 45°, (ii) a straight line L90 indicative of a correlation between Vall and Vmax in a case where a thinned range is 90°, and (iii) a straight line L135 indicative of a correlation between Vall and Vmax in a case where a thinned range is 135°.

Then, intersections, between (i) Vmax obtained by the flaw detection of the magnetic pipe to be inspected and (ii) the straight lines L45, L90, and L135, are calculated. Then, differences between a point corresponding to Vall obtained by the flaw detection of the magnetic pipe to be inspected and the respective intersections are calculated. Then, a thinned range is calculated according to a ratio between the differences.

For example, in a case where values of Vmax and Vall of outer surface local thinning are 0.15 V and 3.8, respectively, values a and b, which are on the straight lines L90 and L135, respectively, and which correspond to Vmax=0.15, are calculated (see FIG. 10). Then, a thinned range is calculated according to a ratio between (b−3.8) and (3.8−a). For example, in a case where a thinned range of thinning to be inspected is X, the thinned range X is calculated according to a relationship "(135−X):(X−90)=(b−3.8):(3.8−a)". In this case, the thinned range is calculated as approximately 100° where Vmax=0.15V and Vall=3.8.

On the other hand, even in a case of outer surface thinning, a thinned range cannot be calculated by the first calculating method if the thinning is local thinning having a narrow thinned range such as a case of thinning where a change in magnetic flux can be detected only by one of eight Hall elements 11. This is because, in such a case, values of Vall fall outside of an evaluation map (e.g. the graph of FIG. 10).

In a case of inner surface thinning, as illustrated in FIG. 9, it is observed that Vall and Vmax are smaller and larger, respectively, than is the case of outer surface thinning. However, unlike the case of outer surface thinning, a clear distribution according to a thinned range along the circumference is not obtained. This is presumably because of the following phenomenon: A space between the Hall elements 11 and the magnetic pipe becomes large directly under the inner surface thinning, and therefore an apparent magnetic resistance increases so as to cause an increase in output signal Vmax. Then, when output voltage values are normalized by the Vmax, the output voltage values become uniformly small.

Therefore, according to the present embodiment, the thinned range calculating section 47 calculates a thinned range not by the first calculating method but by the second calculating method in a case where (i) thinning is outer surface thinning and a value of Vall is less than a certain value (e.g. 3) or (ii) thinning is inner surface thinning. Specifically, in a case of outer surface thinning, the thinned of Vall is a certain value or more in the step S8. In a case where the value of Vall is the certain value or more, the thinned range calculating section 47 calculates a thinned range by the first calculating method in the step S9. In a case where the value of Vall is less than the certain value, the thinned range calculating section 47 calculates a thinned range by the second calculating method in the step S10. In a case of inner surface thinning, the thinned range calculating section 47 calculates a thinned range by the second calculating method in a step S14 described later.

FIG. 11 is a view for describing a calculating method of calculating a thinned range by the second calculating method.

In the second calculating method, one of pieces of thinning formed on a test piece is first extracted as reference thinning. According to the present embodiment, in a case where outer surface thinning is to be measured, thinning having a thinned range of 45° and a thinning rate of 25% is reference thinning. In a case where inner surface thinning is to be measured, thinning having a thinned range of 90° and a thinning rate of 50% (i.e. arc-shaped thinning) is reference thinning. Note that reference thinning can be selected as appropriate from pieces of thinning of a test piece, according to results of a verification experiment conducted in advance.

Then, in a reference profile (see FIG. 11) which is a shape profile of reference thinning (i.e. a profile in which values obtained by normalizing, by Vmax, output voltage values from the Hall elements 11 are connected), an average value of output voltage values from Hall elements 11, which are provided so as to sandwich the Hall element 11 from which Vmax was detected, is set as a reference value. Then, a distance L1, which is a distance between two points corresponding to the reference value in the reference profile, is calculated.

In addition, a distance L2, which is a distance between two points corresponding to the reference value in a shape profile obtained on the basis of the results of flaw detection of a magnetic pipe to be inspected, is calculated. Note that in a case where a width L2 of the shape profile obtained on the basis of the results of the flaw detection of the magnetic pipe is narrower than a width L1 of the reference profile (L1>L2), a virtual profile is obtained in which a point corresponding to Vmax=1 is connected, by a straight line or a curved line, to points corresponding to values obtained by normalizing, by Vmax, the output voltages from the Hall elements 11 which detected. Then, a distance between two points corresponding to the reference value in the virtual profile can be calculated as a distance L2.

Subsequently, a value obtained by multiplying, by L2/L1, a thinned range obtained from the reference profile (45° according to the present embodiment) is calculated as a thinned range of the magnetic pipe to be inspected.

Then, after the thinned range is calculated in the step S9 or the step S10, the thinning depth calculating section 48 calculates a thinning depth based on a thinning deficiency ratio and a thinned range (S11).

Note that a thinning depth d in a case of outer surface thinning can be calculated from $$d = r - \{r^2 - S \cdot 360/(\pi \cdot \theta)\}^{1/2}$$

where (i) r is a radius (mm) of an outer diameter of the magnetic pipe to be inspected, (ii) t is a thickness (mm) of a portion which is intact, (iii) S is a thinning deficiency ratio (%), and (iv) θ is a thinned range (°).

In a case where it is judged in the step S5 that the thinning is not outer surface thinning (but is inner surface thinning), the cross section deficiency ratio calculating section 45 calculates a cross section deficiency ratio Cin according to the above-described cross section deficiency ratio calculating formula for inner surface thinning (S12).

Next, based on the output voltage values from the Hall elements 11, the shape parameter calculating section 46 calculates shape parameters (S13). According to the present embodiment, Vmax and Vall are calculated as shape parameters as in the case of outer surface thinning.

Subsequently, the thinned range calculating section 47 calculates a thinned range by the second calculating method (S14). According to the present embodiment, in a case where inner surface thinning is to be measured, as described above, thinning having a thinned range of 90° and a thinning rate of 50% (i.e. arc-shaped thinning) is reference thinning. Then, a thinned range is calculated by the second calculating method with a shape profile of the reference thinning serving as a reference profile. FIG. 12 is a view for describing a calculating method of calculating a thinned range by the second calculating method.

Then, after the thinned range is calculated in the step S14, the thinning depth calculating section 48 calculates a thinning depth based on a thinning deficiency ratio and a thinned range (S15), and the thinning inspection process ends.

Note that a thinning depth d in a case of inner surface thinning can be calculated from $$d = \{(r-t)^2 + S \cdot 360/(\pi \cdot \theta)\}^{1/2} - (r-t)$$

where (i) r is a radius (mm) of an outer diameter of the magnetic pipe to be inspected, (ii) t is a thickness (mm) of a portion which is intact, (iii) S is a thinning deficiency ratio (%), and (iv) θ is a thinned range (°).

Subsequently, thinned surface judging section 35 judges whether or not the process of calculating cross section deficiency ratios, thinned ranges, and thinning depths for all of positions to be inspected is completed (S16). In a case where there is/are detected position(s) for which the calculation process has not been completed, the thinning inspection process returns to the step S3, and a similar process is repeated. In a case where it is judged in the step S16 that the calculation process has been completed for all of the detected positions, the thinning inspection process ends.

FIG. 13 is a graph showing relationships between (i) thickness evaluated values obtained by measuring pipes used in actual production models by the method in accordance with the present embodiment and (ii) thickness actual values obtained by actually measuring the pipes used in the actual production models. A thickness evaluated value was calculated by (i) calculating a thinning depth of a pipe used in an actual production model by the method in accordance with the present embodiment and (ii) obtaining a difference between the thinning depth thus calculated and a thickness of the pipe while the pipe is intact. A thickness actual value was measured by use of an ultrasonic thickness meter or a submersion rotary ultrasonic thickness measuring method. As illustrated in FIG. 13, it was possible to evaluate the thicknesses by the method in accordance with the present embodiment with an accuracy of approximately ±0.15 mm.

(1-5. Example of Evaluation of Thinning Inspection)

(1-5-1. Example of Evaluation of Inner Surface Thinning)

(a) of FIG. 14 is a graph plotting output voltages from Hall elements 11 in an inspection of an STB pipe (magnetic pipe) which has inner surface thinning and has an outer diameter of 27.2 mm and a thickness of 2.6 mm.

As indicated by (a) of FIG. 14, the thinning is occurring so as to concentrate on part of the pipe along the circumference of the pipe in this example of the evaluation. In addition, in this example of the evaluation, relatively gentle local thinning is occurring such that the output voltages from the Hall elements 11 have only one peak along the circumference.

In this example of the evaluation, a representative thinned portion illustrated in (a) of FIG. 14 was evaluated according to the flow illustrated in FIG. 6, so that the following results were obtained:

<Results of Evaluation of Representative Thinned Portion>

(1) Results of judging thinned surface: inner surface thinning (2) Combined value V_sum of combining output voltages from Hall elements 11: 1.19 V (3) Cross section deficiency ratio S: 16.7% (35.9 mm²) (a=16.163, b=2.5) (4) Thinned range θ along circumference: 110°

(Since the thinning was inner surface thinning, the thinned range θ was calculated by the second calculating method. Specifically, as illustrated in (b) of FIG. 14, L1 and L2 were calculated, and then L2/L1 was calculated as 1.96. Then, by multiplying L2/L1 by the thinned range (56.3°) of a reference thinning, the thinned range θ in the example of the evaluation was calculated as 56.3×1.96≈110°.)

(5) Thinning depth d: 1.6 mm (Since the thinning was inner surface thinning, the thinning depth d was calculated from $$d = \{(r-t)^2 + S \cdot 360/(\pi \cdot \theta)\}^{1/2} - (r-t)$$

(1-5-2. Example of Evaluation of Outer Surface Thinning)

(a) of FIG. 15 is a graph plotting output voltages from Hall elements 11 in an inspection of an STB pipe (magnetic pipe) which has outer surface thinning and has an outer diameter of 25.4 mm and a thickness of 2.0 mm.

In this example of the evaluation, as illustrated in (a) of FIG. 15, corrosion (thinning) was occurring over substantially entire region along the axis of the pipe, and local thinning was occurring at a baffle portion.

In this example of the evaluation, a representative thinned portion was evaluated according to the flow illustrated in FIG. 6, so that the following results were obtained:

<Results of Evaluation of Representative Thinned Portion>

(1) Results of judging thinned surface: outer surface thinning (2) Combined value V_sum of combining output voltages from Hall elements 11: 0.27 V (3) Cross section deficiency ratio S: 4.4% (6.5 mm²) (a=16.163)

(4) Thinned range θ: 51.3°

(Although the thinning was outer surface thinning, the thinned range θ was calculated by the second calculating method because Vall<3.0 V. Specifically, as illustrated in (b) of FIG. 15, L1 and L2 were calculated, and then L2/L1 was calculated as 1.14. Then, by multiplying L2/L1 by the thinned range (45.0°) of a reference thinning, the thinned range θ in the example of the evaluation was calculated as 45.0×1.14≈51.3°.)

(5) Thinning depth d: 0.69 mm (Since the thinning was outer surface thinning, the thinning depth d was calculated from $$d=\{(r-t)^2+S\cdot 360/(\pi\cdot\theta)\}^{1/2}-(r-t)$$

(1-6. Recapitulation)

As has been described, an inspection probe 100 in accordance with the present embodiment includes: a third magnet 4; and Hall elements 11 which are provided on a magnetic circuit formed by the third magnet 4 and a magnetic pipe and which detects a density of a magnetic flux flowing through the magnetic circuit. Thinning of the magnetic pipe is quantitatively evaluated in accordance with output signals from the Hall elements 11 in a case where the inspection probe 100 is moved in the magnetic pipe along an axis of the magnetic pipe. In so doing, the thinning is quantitatively evaluated by applying an evaluation algorithm for inner surface thinning or an evaluation algorithm for outer surface thinning, depending on whether the thinning is occurring on an inner surface side or on a back surface side of the magnetic pipe (i.e. whether the thinning is inner surface thinning or outer surface thinning).

Therefore, it is possible to accurately and quickly carry out a quantitative evaluation of a defect. Specifically, although a conventional magnetization eddy current flaw detection test and a conventional magnetic flux leakage each allow for an inspection of the presence/absence of a defect, it is not possible to quantitatively evaluate the defect. On the other hand, with the method in accordance with the present embodiment, it is possible to accurately carry out a quantitative evaluation of a defect of a magnetic pipe. In addition, although a conventional submersion rotary ultrasonic thickness measuring method allows for a quantitative evaluation of a defect, a speed of an inspection is unfortunately slow. On the other hand, with the method in accordance with the present embodiment, it is possible to quickly carry out a quantitative evaluation of a defect.

According to the present embodiment, the inspection probe 100 includes the yoke 1. However, the inspection probe 100 does not necessarily need to include a yoke 1. Specifically, the inspection probe 100 only needs to be configured so that the magnetic flux density illustrated in FIG. 5 is applied to a magnetic pipe.

According to the present embodiment, the inspection probe 100 is configured so that the second magnet 3 and the third magnet 4 are polarized such that the second magnet 3 and the third magnet 4 face the magnetic pipe P. However, the present invention is not limited to this configuration, provided that the magnetic flux density illustrated in FIG. 5 can be applied to the magnetic pipe P. For example, the second magnet 3 and the third magnet 4 can be provided so that the second magnet 3 and the third magnet 4 are polarized in a direction extending parallel to an axis of a magnetic pipe. In such a case also, Hall elements 11 and the yoke 1 only need to be provided on a magnetic circuit formed by the second magnet 3, the third magnet 4, and the magnetic pipe P.

According to the present embodiment, the inspection probe 100 is inserted into the magnetic pipe P to be inspected, and thinning is measured by the Hall elements 11 while the inspection probe 100 is being moved axially in the magnetic pipe P. However, the present invention is not limited to this configuration. Alternatively, it is possible that the inspection probe 100 is inserted into the magnetic pipe P to be inspected, and then a defect at a certain position of the magnetic pipe P is quantitatively evaluated by measuring an output of a Hall element 11 at the certain position of the magnetic pipe P.

(Other Remarks)

A defect measuring method in accordance with an aspect of the present invention is a method of measuring a defect of a magnetic member, including the steps of: (A) measuring an output from a magnetic sensor with use of an inspection probe including a magnet and the magnetic sensor which is provided on a magnetic circuit formed by the magnet and the magnetic member and which detects a density of a magnetic flux flowing through the magnetic circuit; (B) judging whether the defect is (i) a front surface defect occurring to a front surface of the magnetic member, which front surface is a counter surface facing the inspection probe or (ii) a back surface defect occurring to a back surface of the magnetic member, which back surface is opposite the counter surface; and (C) quantitatively evaluating the defect of the magnetic member by applying, to an output signal from the magnetic sensor, an evaluation algorithm which is selected from evaluation algorithms set in advance for the respective ones of the front surface defect and the back surface defect and which corresponds to a result of the judging in the step (B).

With the method, it is possible to quickly and properly carry out a quantitative evaluation of a defect by the magnetic flux resistance through: measuring an output from a magnetic sensor with use of an inspection probe including a magnet and the magnetic sensor which is provided on a magnetic circuit formed by the magnet and the magnetic member and which detects a density of a magnetic flux flowing through the magnetic circuit; and applying, to the output signal from the magnetic sensor, an evaluation algorithm which is selected according to a result of the judging in the step (B).

The method can be configured so as to further include the step of: (D) carrying out an eddy current test of the magnetic member, in the step (B), whether the defect is present on the front surface or the back surface of the magnetic member is judged in accordance with a result of the eddy current test.

With the configuration, it is possible to quickly and properly carry out a quantitative evaluation of a defect by the magnetic flux resistance through: judging whether the thinning is a front surface defect or a back surface defect by the eddy current test; and applying an evaluation algorithm according to a result of the judging.

The method can be configured so that: the inspection probe includes a plurality of magnets provided so as to form a Halbach array along a counter surface of the inspection probe, which counter surface faces the magnetic member and an eddy current flaw sensor which (i) is provided on part of a magnet provided at a center portion of the Halbach array of the plurality of magnets, which part is located on the counter surface facing the magnetic member and (ii) carries out the eddy current test; and the magnetic sensor is provided on a magnetic circuit formed by the magnetic member and a magnet that is provided at an end part of the Halbach array of the plurality of magnets, and the magnetic sensor detects a density of a magnetic flux flowing through the magnetic circuit.

With the configuration, it is possible to improve operation efficiency because the step (D) and the step (A) can be carried out in parallel.

The method can be configured so that: the magnetic member is a magnetic pipe; and in the step (A), the inspection probe is moved in the magnetic pipe along an axis of the magnetic pipe.

With the method, it is possible to quickly and properly carry out a quantitative evaluation of a defect of a magnetic pipe.

The method can be configured so that: the magnetic sensor outputs a voltage value according to a density of a magnetic flux; the step (C) includes the step of (E) calculating a cross section deficiency ratio that is a ratio of an area of a deficient portion to an area of an entire portion of a cross section perpendicular to the axis of the magnetic pipe; and in the step (E), the cross section deficiency ratio of the magnetic pipe is calculated in accordance with (i) a cross section deficiency ratio calculating formula which is set in advance based on a relationship between (a) a combined value obtained by combining output voltage values from the respective magnetic sensors in a case where a plurality of types of defects formed on a test magnetic pipe are measured by the magnetic sensors and (b) each of actual cross section deficiency ratios of the respective plurality of types of defects formed on the test magnetic pipe and (ii) a combined value obtained by combining output voltage values from the respective magnetic sensors in a case where the magnetic pipe is measured.

With the method, it is possible to quickly and properly calculate a cross section deficiency ratio of a defect of a magnetic pipe.

The method can be configured so that: the step (C) includes the step of (F) calculating a defect range indicative of a range of a defect along a circumference of a cross section perpendicular to the axis of the magnetic pipe; and in the step (F), the defect range of the defect of the magnetic pipe is calculated in accordance with (i) defect range calculating data which is set in advance based on a relationship between (a) a maximum value of output voltage values from the respective magnetic sensors in a case where a plurality of types of defects formed on a test magnetic pipe are measured, (b) a combined value of values obtained by dividing the respective output voltage values by the maximum value, and (c) each of actual defect ranges of the respective plurality of types of defects formed on the test magnetic pipe, (ii) a maximum value of output voltage values from the respective magnetic sensors in a case where the magnetic pipe is measured, and (iii) a combined value of values obtained by dividing the respective output voltage values by the maximum value.

With the method, it is possible to quickly and properly calculate a defect range of a defect of a magnetic pipe.

The method can be configured so that: the step (C) includes the step of (F) calculating a defect range indicative of a range of a defect along a circumference of a cross section perpendicular to the axis of the magnetic pipe; and (G) calculating a depth of the defect occurring to the magnetic pipe; in the step (F), the defect range of the defect of the magnetic pipe is calculated in accordance with (i) defect range calculating data which is set in advance based on a relationship between (a) a maximum value of output voltage values from the respective magnetic sensors in a case where a plurality of types of defects formed on a test magnetic pipe are measured, (b) a combined value of values obtained by dividing the respective output voltage values by the maximum value, and (c) each of actual defect ranges of the respective plurality of types of defects formed on the test magnetic pipe, (ii) a maximum value of output voltage values from the respective magnetic sensors in a case where the magnetic pipe is measured, and (iii) a combined value of values obtained by dividing the respective output voltage values by the maximum value; and in the step (G), the depth of the defect is calculated in accordance with $d=r-\{r^2-S\cdot 360/(\pi\cdot\theta)\}^{1/2}$ in a case where the defect is present on the back surface of the magnetic pipe, which back surface is opposite the counter surface facing the inspection probe and in accordance with $d=\{(r-t)^2+S\cdot 360/(\pi\cdot\theta)\}^{1/2}-(r-t)$ in a case where the defect is present on the front surface of the magnetic pipe, which front surface is the counter surface facing the inspection probe, where (i) r is a radius (mm) of an outer diameter of the magnetic pipe, (ii) S is the cross section deficiency ratio (%) calculated in the step (E), (iii) θ is the defect range (°) calculated in the step (F), and (iv) d is the depth (mm) of the defect.

With the method, it is possible to quickly and properly calculate a depth of a defect of a magnetic pipe.

A defect measuring device in accordance with an aspect of the present invention is a defect measuring device which measures a defect of a magnetic member, including: an inspection probe including a magnet and a magnetic sensor which is provided on a magnetic circuit formed by the magnet and the magnetic member and which detects a density of a magnetic flux flowing through the magnetic circuit; and a magnetic flux resistance computing section which is capable of quantitatively evaluating the defect of the magnetic member in accordance with an output signal from the magnetic sensor, the magnetic flux resistance computing section being capable of quantitatively evaluating the defect of the magnetic member by applying, to the output signal, an evaluation algorithm which is selected according to whether (i) the defect is formed on a front surface of the magnetic member, which front surface is a counter surface facing the inspection probe or (ii) the defect is formed on a back surface which is opposite the counter surface.

With the configuration, it is possible to quickly and properly carry out a quantitative evaluation of a defect by the magnetic flux resistance through, with use of an inspection probe including a magnet and a magnetic sensor which is provided on a magnetic circuit formed by the magnet and the magnetic member and which detects a density of a magnetic flux flowing through the magnetic circuit, applying, to an output signal from the magnetic sensor, an evaluation algorithm which is selected according to which of the front surface and the back surface of the magnetic member has a defect.

The defect measuring device can be configured so that: the inspection probe includes a plurality of magnets provided so as to form a Halbach array along a counter surface of the inspection probe, which counter surface faces the magnetic member, an eddy current flaw sensor provided at a center portion of the Halbach array of the plurality of magnets, a magnetic sensor which (i) is provided on a magnetic circuit formed by the magnetic member and a magnet that is provided at an end part of the Halbach array of the plurality of magnets and (ii) detects a density of a magnetic flux flowing through the magnetic circuit, and a defect surface judging section which is capable of judging, based on a result of an eddy current test with use of the eddy current flaw sensor, which of the front surface and the back surface of the magnetic member has the defect, and the magnetic flux resistance computing section is capable of quantitatively evaluating the defect of the magnetic member by applying, to the output signal, an evaluation algorithm which is selected according to a result of the judging by the defect surface judging section.

With the configuration, it is possible to improve operation efficiency because measurement by the eddy current flaw sensor and the measurement by the magnetic sensor can be carried out in parallel.

The defect measuring device can be configured so that: the magnetic member is a magnetic pipe; and the magnetic flux resistance computing section is capable of quantitatively evaluating the defect of the magnetic pipe in accordance with output signals supplied from respective ones of magnetic sensors while the inspection probe is moved in the magnetic pipe along an axis of the magnetic pipe.

With the configuration, it is possible to quickly and properly carry out a quantitative evaluation of a defect of a magnetic pipe.

The defect measuring device can be configured so that: the magnetic sensor outputs a voltage value according to a density of a magnetic flux; the magnetic flux resistance computing section includes a cross section deficiency ratio calculating section capable of calculating a cross section deficiency ratio that is a ratio of an area of a deficient portion to an area of an entire portion of a cross section perpendicular to the axis of the magnetic pipe; and the cross section deficiency ratio calculating section is capable of calculating the cross section deficiency ratio of the magnetic pipe in accordance with (i) a cross section deficiency ratio calculating formula which is set in advance based on a relationship between (a) a combined value obtained by combining output voltage values from the respective magnetic sensors in a case where a plurality of types of defects formed on a test magnetic pipe are measured by the magnetic sensors and (b) each of actual cross section deficiency ratios of the respective plurality of types of defects formed on the test magnetic pipe and (ii) a combined value obtained by combining output voltage values from the respective magnetic sensors in a case where the magnetic pipe is measured.

With the configuration, it is possible to quickly and properly calculate a cross section deficiency ratio of a defect of a magnetic pipe.

The defect measuring device can be configured so that: the magnetic flux resistance computing section includes a defect range calculating section which is capable of calculating a defect range indicative of a range of a defect along the circumference of a cross section perpendicular to the axis of the magnetic pipe; and the defect range calculating section is capable of calculating the defect range of the magnetic pipe in accordance with (i) defect range calculating data which is set in advance based on a relationship between (a) a maximum value of output voltage values from the respective magnetic sensors in a case where a plurality of types of defects formed on a test magnetic pipe are measured, (b) a combined value of values obtained by dividing the respective output voltage values by the maximum value, and (c) each of actual defect ranges of the respective plurality of types of defects formed on the test magnetic pipe, (ii) a maximum value of output voltage values from the respective magnetic sensors in a case where the magnetic pipe is measured, and (iii) a combined value of values obtained by dividing the respective output voltage values by the maximum value.

With the configuration, it is possible to quickly and properly calculate a defect range of a defect of a magnetic pipe.

The defect measuring device can be configured so that: the magnetic flux resistance computing section includes a defect range calculating section which is capable of calculating a defect range indicative of a range of a defect along a circumference of a cross section perpendicular to the axis of the magnetic pipe and a defect depth calculating section which calculates a depth of the defect occurring to the magnetic pipe; the defect range calculating section is capable of calculating the defect range of the magnetic pipe in accordance with (i) defect range calculating data which is set in advance based on a relationship between (a) a maximum value of output voltage values from the respective magnetic sensors in a case where a plurality of types of defects formed on a test magnetic pipe are measured, (b) a combined value of values obtained by dividing the respective output voltage values by the maximum value, and (c) each of actual defect ranges of the respective plurality of types of defects formed on the test magnetic pipe, (ii) a maximum value of output voltage values from the respective magnetic sensors in a case where the magnetic pipe is measured, and (iii) a combined value of values obtained by dividing the respective output voltage values by the maximum value; and the defect depth calculating section is capable of calculating the depth of the defect in accordance with $d=r-\{r^2-S\cdot360/(\pi\cdot\theta)\}^{1/2}$ in a case where the defect is present on the back surface of the magnetic pipe, which back surface is opposite the counter surface facing the inspection probe and in accordance with $d=\{(r-t)^2+S\cdot360/(\pi\cdot\theta)\}^{1/2}-(r-t)$ in a case where the defect is present on the front surface of the magnetic pipe, which front surface is the counter surface facing the inspection probe, where (i) r is a radius (mm) of an outer diameter of the magnetic pipe, (ii) S is the cross section deficiency ratio (%) calculated by the cross section deficiency ratio calculating section, (iii) $\theta$ is the defect range (°) calculated by the defect range calculating section, and (iv) d is the depth (mm) of the defect.

With the configuration, it is possible to quickly and properly calculate a depth of a defect of a magnetic pipe.

An inspection probe in accordance with an aspect of the present invention is an inspection probe which inspects a defect of a magnetic member, including: a plurality of magnets provided so as to form a Halbach array along a counter surface of the inspection probe, which counter surface faces the magnetic member; an eddy current flaw sensor provided at a center portion of the Halbach array of the plurality of magnets; and a magnetic sensor which (i) is provided on a magnetic circuit formed by the magnetic member and a magnet that is provided at an end part of the Halbach array of the plurality of magnets and (ii) detects a density of a magnetic flux flowing through the magnetic circuit.

With the configuration, it is possible to (i) judge, based on the result of the eddy current flaw sensor, whether the defect of the magnetic member is present on the counter surface facing the inspection probe or is present on the back surface opposite the counter surface and (ii) quantitatively evaluate, based on the result of the detection by the magnetic sensor, the defect by the magnetic flux resistance. In addition, because measurement data of the eddy current flaw sensor and measurement data of the magnetic sensor can be obtained in parallel, it is possible to improve operation efficiency.

The inspection probe can be configured so as to further include: a yoke which is a cylindrical member made of a magnetic material, the plurality of magnets being provided (i) so as to form a Halbach array along an axis of the yoke and) in a cylindrical form along an outer circumferential surface of the yoke, and a plurality of the magnetic sensors being provided along a circumference of the yoke.

With the configuration, it is possible to quickly and properly carry out a quantitative evaluation of a defect of a magnetic pipe.

(Additional Remarks)

The present invention is not limited to the description of the embodiments, but can be altered in many ways by a person skilled in the art within the scope of the claims. An embodiment derived from a proper combination of technical means disclosed in different embodiments is also encompassed in the technical scope of the present invention.

INDUSTRIAL APPLICABILITY

The present invention can be applied to (i) a method and a device for measuring a defect of a member made of a magnetic material and (iii) an inspection probe for use in measurement of the defect.

REFERENCE SIGNS LIST

1 Yoke
2 First magnet
3 Second magnet
4 Third magnet
5 Excitation and detection coil (eddy current flaw sensor)
11 Hall element (magnetic sensor)
20 Thinning judging section (defect judging section)
30 Eddy current flaw detecting section
31 First detecting section
32 First storage section
33 Eddy current flow computing section
34 Detected position identifying section
35 Thinned surface judging section (defect surface judging section)
40 Magnetic flux resistance flaw detecting section
41 Second detecting section
42 Second storage section
34 Magnetic flux resistance computing section
44 Detected position identifying section
45 Cross section deficiency ratio calculating section
46 Shape parameter calculating section
47 Thinning range calculating section (defect range calculating section)
48 Calculating section
100 Inspection probe
200 Thinning measuring device (defect measuring device)
P Magnetic pipe (magnetic member)

The invention claimed is:

1. A method of measuring a defect of a magnetic member, comprising the steps of:
   (A) measuring an output from a magnetic sensor with use of an inspection probe including a magnet, the magnetic sensor which is provided on a magnetic circuit formed by the magnet and the magnetic member and which detects a density of a magnetic flux flowing through the magnetic circuit, and an excitation and detection coil which excites an eddy current for an eddy current test;
   (B) judging, by the eddy current test based on the eddy current excited by the excitation and detection coil, whether the defect is (i) a front surface defect occurring to a front surface of the magnetic member, which front surface is a counter surface facing the inspection probe or (ii) a back surface defect occurring to a back surface of the magnetic member, which back surface is opposite the counter surface; and
   (C) quantitatively evaluating the defect of the magnetic member by applying, to an output signal from the magnetic sensor, an evaluation algorithm which is selected from evaluation algorithms set in advance for the respective ones of the front surface defect and the back surface defect and which corresponds to a result of the judging in the step (B).

2. The method as set forth in claim 1, wherein:
the inspection probe includes
   a plurality of magnets provided so as to form a Halbach array along a counter surface of the inspection probe, which counter surface faces the magnetic member;
   the excitation and detection coil is provided on part of a magnet provided at a center portion of the Halbach array of the plurality of magnets, which part is located on the counter surface facing the magnetic member; and
the magnetic sensor is provided on a magnetic circuit formed by the magnetic member and a magnet that is provided at an end part of the Halbach array of the plurality of magnets, and the magnetic sensor detects a density of a magnetic flux flowing through the magnetic circuit.

3. The method as set forth in claim 1, wherein:
the magnetic member is a magnetic pipe; and
in the step (A), the inspection probe is moved in the magnetic pipe along an axis of the magnetic pipe.

4. The method as set forth in claim 3, wherein:
the magnetic sensor outputs a voltage value according to a density of a magnetic flux;
the step (C) includes the step of
(E) calculating a cross section deficiency ratio that is a ratio of an area of a deficient portion to an area of an entire portion of a cross section perpendicular to the axis of the magnetic pipe; and
in the step (E), the cross section deficiency ratio of the magnetic pipe is calculated in accordance with (i) a cross section deficiency ratio calculating formula which is set in advance based on a relationship between (a) a combined value obtained by combining output voltage values from the respective magnetic sensors in a case where a plurality of types of defects formed on a test magnetic pipe are measured by the magnetic sensors and (b) each of actual cross section deficiency ratios of the respective plurality of types of defects formed on the test magnetic pipe and (ii) a combined value obtained by combining output voltage values from the respective magnetic sensors in a case where the magnetic pipe is measured.

5. The method as set forth in claim 3, wherein:
the step (C) includes the step of (F) calculating a defect range indicative of a range of a defect along a circumference of a cross section perpendicular to the axis of the magnetic pipe; and
in the step (F), the defect range of the defect of the magnetic pipe is calculated in accordance with (i) defect range calculating data which is set in advance based on a relationship between (a) a maximum value of output voltage values from the respective magnetic sensors in a case where a plurality of types of defects formed on a test magnetic pipe are measured, (b) a combined value of values obtained by dividing the respective output voltage values by the maximum value, and (c) each of actual defect ranges of the respective plurality of types of defects formed on the test magnetic pipe, (ii) a maximum value of output voltage values from the respective magnetic sensors in a case where the magnetic pipe is measured, and (iii) a combined value of values obtained by dividing the respective output voltage values by the maximum value.

6. The method as set forth in claim 4, wherein:
the step (C) includes the steps of
(F) calculating a defect range indicative of a range of a defect along a circumference of a cross section perpendicular to the axis of the magnetic pipe and
(G) calculating a depth of the defect occurring to the magnetic pipe;
in the step (F), the defect range of the defect of the magnetic pipe is calculated in accordance with (i) defect range calculating data which is set in advance based on a relationship between (a) a maximum value of output voltage values from the respective magnetic sensors in a case where a plurality of types of defects formed on a test magnetic pipe are measured, (b) a combined value of values obtained by dividing the respective output voltage values by the maximum value, and (c) each of actual defect ranges of the respective plurality of types of defects formed on the test magnetic pipe, (ii) a maximum value of output voltage values from the respective magnetic sensors in a case where the magnetic pipe is measured, and (iii) a combined value of values obtained by dividing the respective output voltage values by the maximum value; and
in the step (G), the depth of the defect is calculated in accordance with $$d=r-\{r^2-S\cdot 360/(\pi\cdot\theta)\}^{1/2}$$

in a case where the defect is present on the back surface of the magnetic pipe, which back surface is opposite the counter surface facing the inspection probe and
in accordance with $$d=\{(r-t)^2+S\cdot 360/(\pi\cdot\theta)\}^{1/2}-(r-t)$$

in a case where the defect is present on the front surface of the magnetic pipe, which front surface is the counter surface facing the inspection probe,
where (i) r is a radius (mm) of an outer diameter of the magnetic pipe, (ii) S is the cross section deficiency ratio (%) calculated in the step (E), (iii) θ is the defect range (°) calculated in the step (F), and (iv) d is the depth (mm) of the defect.

7. A defect measuring device which measures a defect of a magnetic member, comprising:
an inspection probe including
a magnet,
a magnetic sensor which is provided on a magnetic circuit formed by the magnet and the magnetic member and which detects a density of a magnetic flux flowing through the magnetic circuit, and
an excitation and detection coil which excites an eddy current for an eddy current test;
an eddy current flow computing section which makes a judgment, on the basis of a detection signal from the excitation and detection coil, as to whether (i) the defect is formed on a front surface of the magnetic member, which front surface is a counter surface facing the inspection probe or (ii) the defect is formed on a back surface which is opposite the counter surface; and
a magnetic flux resistance computing section which is capable of quantitatively evaluating the defect of the magnetic member in accordance with an output signal from the magnetic sensor,
the magnetic flux resistance computing section being capable of quantitatively evaluating the defect of the magnetic member by applying, to the output signal, an evaluation algorithm which is selected according to a result of the judgment made by the eddy current flow computing section.

8. The defect measuring device as set forth in claim 7, wherein:
the inspection probe includes
a plurality of magnets provided so as to form a Halbach array along a counter surface of the inspection probe, which counter surface faces the magnetic member,
the excitation and detection coil is provided at a center portion of the Halbach array of the plurality of magnets,
the magnetic sensor (i) is provided on a magnetic circuit formed by the magnetic member and a magnet, as a part of the Halbach-arrayed magnets, that is provided at an end part of the Halbach array of the plurality of magnets and (ii) detects a density of a magnetic flux flowing through the magnetic circuit,
the inspection probe further includes
a defect surface judging section which is capable of judging, based on a result of an eddy current test with use of the excitation and detection coil, which of the front surface and the back surface of the magnetic member has the defect, and
the magnetic flux resistance computing section is capable of quantitatively evaluating the defect of the magnetic member by applying, to the output signal, an evaluation algorithm which is selected according to a result of the judging by the defect surface judging section.

9. The defect measuring device as set forth in claim 7, wherein:
the magnetic member is a magnetic pipe; and
the magnetic flux resistance computing section is capable of quantitatively evaluating the defect of the magnetic pipe in accordance with output signals supplied from respective ones of magnetic sensors while the inspection probe is moved in the magnetic pipe along an axis of the magnetic pipe.

10. The defect measuring device as set forth in claim 9, wherein:
the magnetic sensor outputs a voltage value according to a density of a magnetic flux;
the magnetic flux resistance computing section includes
a cross section deficiency ratio calculating section capable of calculating a cross section deficiency ratio that is a ratio of an area of a deficient portion to an area of an entire portion of a cross section perpendicular to the axis of the magnetic pipe; and
the cross section deficiency ratio calculating section is capable of calculating the cross section deficiency ratio of the magnetic pipe in accordance with (i) a cross section deficiency ratio calculating formula which is set in advance based on a relationship between (a) a combined value obtained by combining output voltage values from the respective magnetic sensors in a case where a plurality of types of defects formed on a test magnetic pipe are measured by the magnetic sensors and (b) each of actual cross section deficiency ratios of the respective plurality of types of defects formed on the test magnetic pipe and (ii) a combined value obtained by combining output voltage values from the respective magnetic sensors in a case where the magnetic pipe is measured.

11. The defect measuring device as set forth in claim 9, wherein:

the magnetic flux resistance computing section includes
a defect range calculating section which is capable of calculating a defect range indicative of a range of a defect along the circumference of a cross section perpendicular to the axis of the magnetic pipe; and the defect range calculating section is capable of calculating the defect range of the magnetic pipe in accordance with (i) defect range calculating data which is set in advance based on a relationship between (a) a maximum value of output voltage values from the respective magnetic sensors in a case where a plurality of types of defects formed on a test magnetic pipe are measured, (b) a combined value of values obtained by dividing the respective output voltage values by the maximum value, and (c) each of actual defect ranges of the respective plurality of types of defects formed on the test magnetic pipe, (ii) a maximum value of output voltage values from the respective magnetic sensors in a case where the magnetic pipe is measured, and (iii) a combined value of values obtained by dividing the respective output voltage values by the maximum value.

12. The defect measuring device as set forth in claim 10, wherein:

the magnetic flux resistance computing section includes
a defect range calculating section which is capable of calculating a defect range indicative of a range of a defect along a circumference of a cross section perpendicular to the axis of the magnetic pipe and
a defect depth calculating section which calculates a depth of the defect occurring to the magnetic pipe;

the defect range calculating section is capable of calculating the defect range of the magnetic pipe in accordance with (i) defect range calculating data which is set in advance based on a relationship between (a) a maximum value of output voltage values from the respective magnetic sensors in a case where a plurality of types of defects formed on a test magnetic pipe are measured, (b) a combined value of values obtained by dividing the respective output voltage values by the maximum value, and (c) each of actual defect ranges of the respective plurality of types of defects formed on the test magnetic pipe, (ii) a maximum value of output voltage values from the respective magnetic sensors in a case where the magnetic pipe is measured, and (iii) a combined value of values obtained by dividing the respective output voltage values by the maximum value; and the defect depth calculating section is capable of calculating the depth of the defect
in accordance with $$d = r - \{r^2 - S \cdot 360/(\pi \cdot \theta)\}^{1/2}$$

in a case where the defect is present on the back surface of the magnetic pipe, which back surface is opposite the counter surface facing the inspection probe and
in accordance with $$d = \{(r-t)^2 + S \cdot 360/(\pi \cdot \theta)\}^{1/2} - (r-t)$$

in a case where the defect is present on the front surface of the magnetic pipe, which front surface is the counter surface facing the inspection probe, where (i) r is a radius (mm) of an outer diameter of the magnetic pipe, (ii) S is the cross section deficiency ratio (%) calculated by the cross section deficiency ratio calculating section, (iii) θ is the defect range)(° calculated by the defect range calculating section, and (iv) d is the depth (mm) of the defect.

13. An inspection probe which inspects a defect of a magnetic member, comprising:

a plurality of magnets provided so as to form a Halbach array along a counter surface of the inspection probe, which counter surface faces the magnetic member;

an excitation and detection coil which is provided at a center portion of the Halbach array of the plurality of magnets and excites an eddy current for an eddy current test; and a magnetic sensor which (i) is provided on a magnetic circuit formed by the magnetic member and a magnet, as a part of the Halbach-arrayed magnets, that is provided at an end part of the Halbach array of the plurality of magnets and (ii) detects a density of a magnetic flux flowing through the magnetic circuit.

14. The inspection probe as set forth in claim 13, further comprising:

a yoke which is a cylindrical member made of a magnetic material, the plurality of magnets being provided (i) so as to form a Halbach array along an axis of the yoke and (ii) in a cylindrical form along an outer circumferential surface of the yoke, and a plurality of the magnetic sensors being provided along a circumference of the yoke.

* * * * *